(12) United States Patent
Wolfe

(10) Patent No.: US 7,109,295 B2
(45) Date of Patent: Sep. 19, 2006

(54) ZINC FINGER-BASED DRUG-DEPENDENT GENE REGULATION SYSTEM

(75) Inventor: Scot Andrew Wolfe, Winchester, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/497,901

(22) PCT Filed: Dec. 9, 2002

(86) PCT No.: PCT/US02/39122

§ 371 (c)(1),
(2), (4) Date: Sep. 22, 2004

(87) PCT Pub. No.: WO03/054148

PCT Pub. Date: Jul. 3, 2003

(65) Prior Publication Data

US 2005/0042732 A1    Feb. 24, 2005

Related U.S. Application Data

(60) Provisional application No. 60/338,407, filed on Dec. 7, 2001.

(51) Int. Cl.
*A61K 15/09* (2006.01)
*C12P 29/00* (2006.01)

(52) U.S. Cl. .................. 530/350; 530/387.3; 514/2; 435/69.7; 435/440; 424/185.1

(58) Field of Classification Search ............... 530/350, 530/378.3, 387.3; 514/2; 424/185.1; 435/185.1
See application file for complete search history.

(56) References Cited

U.S. PATENT DOCUMENTS 6,136,954 A * 10/2000 Bujard et al. ............... 530/350
6,271,348 B1 * 8/2001 Bujard et al. ............... 530/350

FOREIGN PATENT DOCUMENTS

WO    WO 9601313 A1 *  1/1996

OTHER PUBLICATIONS

Numoto et al. (1999) ZF5, which is a Kruppel-type transcriptional repressor, requires the zinc finger domain for self-association. Biochem. Biophys. Res. Commun. vol. 256, No. 3, pp. 573-578.*
Englert, C. (1998) WT1—more than a transcription factor? Trends Biochem. Sci. vol. 23, No. 10, pp. 389-393.*
Blau and Rossi, "Tet B or not tet B: Advances in tetracycline-inducible gene expression," *Proc. Natl. Acad. Sci. USA*, 96:797-799 (1999).
Deuschle et al., "Tetracycline-Reversible Silencing of Eukaryotic Promoters," *Mol. Cell. Biol.*, 15(4):1907-1914 (1995).
Forster et al., "Tetracycline-inducible expression systems with reduced basal activity in mammalian cells," *Nucleic Acids Res.*, 27(2):708-710 (1999).
Looman et al., "KRAB Zinc Finger Proteins: An Analysis of the Molecular Mechanisms Governing Their Increase in Numbers and Complexity During Evolution," *Mol. Biol. Evol.*, 19(12):2118-2130 (2002).
Maxwell and Maxwell, "Control of parvovirus DNA replication by a tetracycline-regulated repressor," *Gene Ther.*, 6:309-313 (1999).
Nakayama et al., "Tetracycline-Regulatable System To Tightly Control Gene Expression in the Pathogenic Fungus *Candida albicans*," *Infect. Immun.*, 68(12):6712-6719 (2000).
Peng et al., "Biochemical Analysis of the Kruppel-associated Box (KRAB) Transcriptional Repression Domain," *J. Biol. Chem.*, 275(24):18000-18010 (2000).
Ryan et al., "KAP-1 Corepressor Protein Interacts and Colocalizes with Heterochromatic and Euchromatic HP1 Proteins: a Potential Role for Krüppel-Associated Box-Zinc Finger Proteins in Heterochromatin-Mediated Gene Silencing," *Mol. Cell. Biol.*, 19(6):4366-4378 (1999).
Abraham and Wiederrecht, "Immunopharmacology of rapamycin," J. Ann. Rev. Immunol. 14:483-510 (1996).
Beerli et al., "Positive and negative regulation of endogenous genes by designed transcription factors," Proc. Natl. Acad. Sci. USA 97(4):1495-500 (2000).
Beerli et al., "Chemically regulated zinc finger transcription factors," J. Biol. Chem. 275(42):32617-627 (2000).
Clemons et al., "Synthesis of calcineurin-resistant derivatives of FK506 and selection of compensatory receptors," Chem. Biol. 9(1):49-61 (2002).
Coward et al., "4-Hydroxytamoxifen binds to and deactivates the estrogen-related receptor gamma," Proc. Natl. Acad. Sci. USA. 98(15):8880-84 (2001).
Detmar et al., "Increased microvascular density and enhanced leukocyte rolling adhesion in the skin of VEGF transgenic mice," J. Invest. Dermatol. 111(1):1-6 (1998).
Elrod-Erickson, "Zif268 protein-DNA complex refined at 1.6 Å: a model system for understanding zinc finger-DNA interactions," Structure 4(10):1171-80 (1996).
Elson et al., "Induction of hypervascularity without leakage or inflammation in transgenic mice overexpressing hypoxia-inducible factor-1alpha," Genes Dev. 15(19):2520-32(2001).

(Continued)

*Primary Examiner*—Jon Weber
*Assistant Examiner*—Samuel Liu
(74) *Attorney, Agent, or Firm*—Fish & Richardson P.C.

(57) ABSTRACT

The invention is related to a fusion polypeptide involving transcription regulation of a target gene. Said fusion polypeptide consists of (i) a zinc finger domain that recognizes and binds to the corresponding nucleic acid recognition sequence in the vicinity of a promoter of the target gene; (ii) a dimerization domain of a tetracycline (tet) repressor which contains a drug (e.g., tetracycline)-dependent switch, and (iii) an accessory domain which alters the expression of the target gene (such as an transcriptional activation or repression domain). This fusion polypeptide can be administered to, or expressed in, a cell harboring the target gene to be regulated.

17 Claims, 6 Drawing Sheets

OTHER PUBLICATIONS

Gossen et al., "Transcriptional activation by tetracyclines in mammalian cells," Science 268(5218):1766-9 (1995).

Hinrichs et al., "Structure of the Tet repressor-tetracycline complex and regulation of antibiotic resistance," Science 264(5157):418-20 (1994).

Kim et al., "A 2.2 Å resolution crystal structure of a designed zinc finger protein bound to DNA," Nat. Struct. Biol. 3(11):940-5 (1996).

Larcher et al., "VEGF/VPF overexpression in skin of transgenic mice induces angiogenesis, vascular hyperpermeability and accelerated tumor development," Oncogene 17(3):303-11 (1998).

Liu et al., "Regulation of an endogenous locus using a panel of designed zinc finger proteins targeted to accessible chromatin regions. Activation of vascular endothelial growth factor A," J. Biol. Chem. 276(14):11323-34 (2001).

Liu et al., "Validated zinc finger protein designs for all 16 GNN DNA triplet targets," J. Biol. Chem. 277(6):3850-6 (2002).

Orth et al., "Structural basis of gene regulation by the tetracycline inducible Tet repressor-operator system," Nat. Struct. Biol. 7(3):215-19 (2000).

Pabo et al., "Design and selection of novel $Cys_2His_2$ zinc finger proteins," Annu. Rev. Biochem. 70:313-40 (2001).

Pomerantz et al., "Structure-based design of transcription factors," Science 267(5194):93-96 (1995).

Pomerantz, "Structure-based design of a dimeric zinc finger protein," Biochemistry 37(4):965-70 (1998).

Rebar et al., "Induction of angiogenesis in a mouse model using engineered transcription factors," Nat. Med. 8(12):1427-32 (2002).

Rivera et al., "A humanized system for pharmacologic control of gene expression," Nat. Med. 2(9):1028-32 (1996).

Saenger, "The Tetracycline Repressor—A Paradigm for a Biological Switch," Angew Chem. Int. Ed. Engl. 39(12):2042-2052 (2000).

Stemmer, "Rapid evolution of a protein in vitro by DNA shuffling," Nature 370(6488):389-91 (1994).

Thurston et al., "Leakage-resistant blood vessels in mice transgenically overexpressing angiopoietin-1," Science 286(5449):2511-4 (1999).

Urlinger et al., "Exploring the sequence space for tetracycline-dependent transcriptional activators: novel mutations yield expanded range and sensitivity," Proc. Natl. Acad. Sci. USA 97(14):7963-8 (2000).

Wolfe et al., "DNA recognition by $Cys_2His_2$ zinc finger proteins," Annu. Rev. Biophys. Biomol. Struct. 29:183-212 (2000).

Wolfe et al., "Beyond the "recognition code": structures of two Cys2His2 zinc finger/TATA box complexes," Structure (Camb) 9(8):717-23 (2001).

Wolfe et al., "Combining structure-based design with phage display to create new $Cys_2His_2$ zinc finger dimers," Structure Fold. Des. 8(7):739-50 (2000).

Xu et al., "A versatile framework for the design of ligand-dependent, transgene-specific transcription factors," Mol. Ther. 3(2):262-73 (2001).

Ye et al., "Regulated delivery of therapeutic proteins after in vivo somatic cell gene transfer," Science 283(5398):88-91 (1999).

Zhang et al., "Synthetic zinc finger transcription factor action at an endogenous chromosomal site. Activation of the human erythropoietin gene," J. Biol. Chem. 275(43):33850-60 (2000).

* cited by examiner

```
1/1                                        31/11
ATG GCC TCC GGG CCC TTC CAG TGT CGA ATC TGC ATG CGT AAC TTC AGT CGT AGT GAC CAC
 M   A   S   G   P   F   Q   C   R   I   C   M   R   N   F   S   R   S   D   H

61/21                                      91/31
CTT ACC ACC CAC ATC cGC ACC CAC ACA GGC GAG AAG CCT TTT GCC TGT GAC ATT TGT GGG
 L   T   T   H   I   R   T   H   T   G   E   K   P   F   A   C   D   I   C   G

121/41                                     151/51
AGG AAG TTT GCC AGG AGT GAT GAA CGC AAG CGT CAT ACC AAA ATC CAT ACA AGC ATC ATC
 R   K   F   A   R   S   D   E   R   K   R   H   T   K   I   H   T   S   I   I

181/61                                     211/71
GCG CGG GTG ACG AAG CGG GCT TTG CTC GAC GCC TTA GCC ATT GAG ATG TTA GAT AGG CAC
 A   R   V   T   K   R   A   L   L   D   A   L   A   I   E   M   L   D   R   H

241/81                                     271/91
CAT ACT CAC TTT TGC CCT TTA GAA GGG GAA AGC TGG CAA GAT TTT TTA CGT AAT AAC GCT
 H   T   H   F   C   P   L   E   G   E   S   W   Q   D   F   L   R   N   N   A

301/101                                    331/111
AAA AGT TTT AGA TGT GCT TTA CTA AGT CAT CGC GAT GGA GCA AAA GTA CAT TTA GGT ACA
 K   S   F   R   C   A   L   L   S   H   R   D   G   A   K   V   H   L   G   T

361/121                                    391/131
CGG CCT ACA GAA AAA CAG TAT GAA ACT CTC GAA AAT CAA TTA GCC TTT TTA TGC CAA CAA
 R   P   T   E   K   Q   Y   E   T   L   E   N   Q   L   A   F   L   C   Q   Q

421/141                                    451/151
GGT TTT TCA CTA GAG AAT GCA TTA TAT GCA CTC AGC GCT GTG GGG CAT TTT ACT TTA GGT
 G   F   S   L   E   N   A   L   Y   A   L   S   A   V   G   H   F   T   L   G

481/161                                    511/171
TGC GTA TTG GAA GAT CAA GAG CAT CAA GTC GCT AAA GAA GAA AGG GAA ACA CCT ACT ACT
 C   V   L   E   D   Q   E   H   Q   V   A   K   E   E   R   E   T   P   T   T

541/181                                    571/191
GAT AGT ATG CCG CCA TTA TTA CGA CAA GCT ATC GAA TTA TTT GAT CAC CAA GGT GCA GAG
 D   S   M   P   P   L   L   R   Q   A   I   E   L   F   D   H   Q   G   A   E

601/201                                    631/211
CCA GCC TTC TTA TTC GGC CTT GAA TTG ATC ATA TGC GGA TTA GAA AAA CAA CTT AAA TGT
 P   A   F   L   F   G   L   E   L   I   I   C   G   L   E   K   Q   L   K   C

661/221
GAA AGT GGG TCT AGA GAC TAG    (SEQ ID NO:1)
 E   S   G   S   R   D   *     (SEQ ID NO:2)
```

FIG. 3

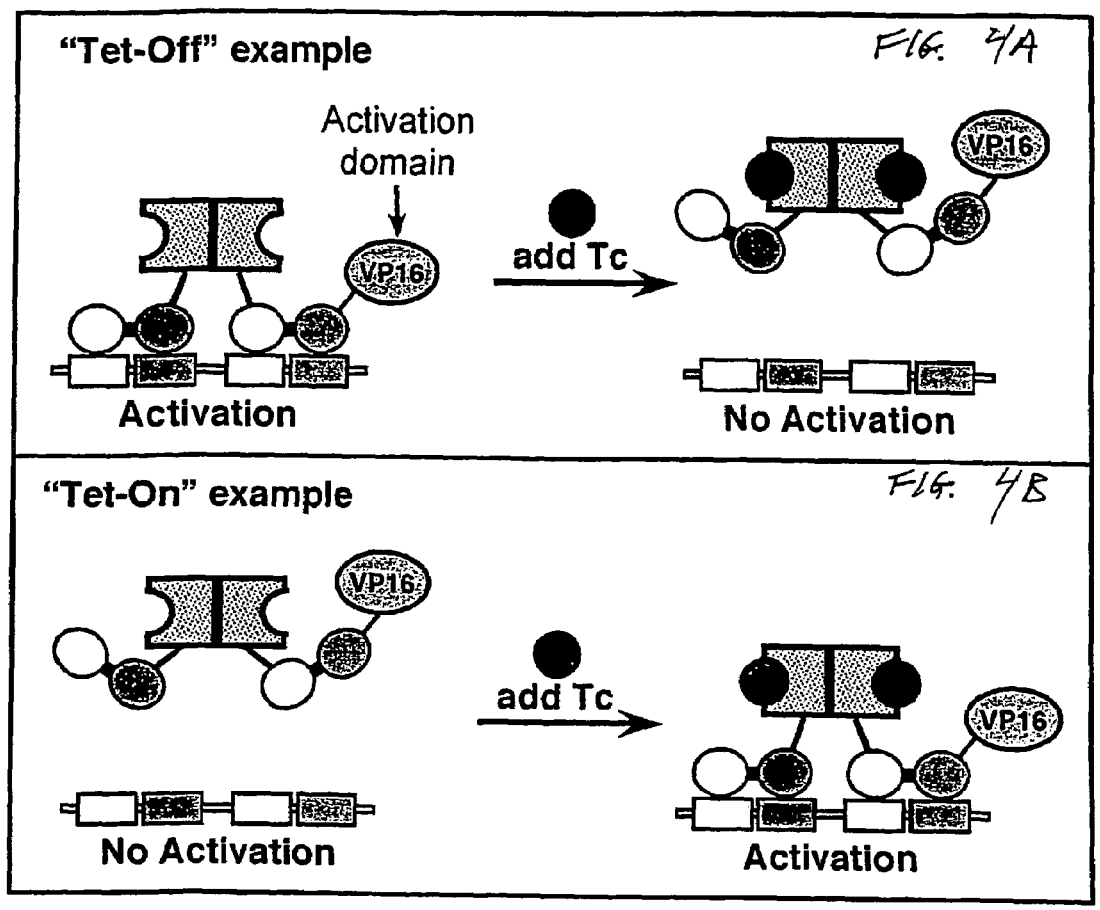

SEQUENCE LISTING

```
<160> NUMBER OF SEQ ID NOS: 21

<210> SEQ ID NO 1
<211> LENGTH: 678
<212> TYPE: DNA
<213> ORGANISM: Artificial Sequence
<220> FEATURE:
<223> OTHER INFORMATION: ZF-TetR-DD clone
<220> FEATURE:
<221> NAME/KEY: CDS
<222> LOCATION: (1)...(675)

<400> SEQUENCE: 1 atg gcc tcc ggg ccc ttc cag tgt cga atc tgc atg cgt aac ttc agt        48
Met Ala Ser Gly Pro Phe Gln Cys Arg Ile Cys Met Arg Asn Phe Ser
 1               5                  10                  15 cgt agt gac cac ctt acc acc cac atc cgc acc cac aca ggc gag aag        96
Arg Ser Asp His Leu Thr Thr His Ile Arg Thr His Thr Gly Glu Lys
             20                  25                  30 cct ttt gcc tgt gac att tgt ggg agg aag ttt gcc agg agt gat gaa       144
Pro Phe Ala Cys Asp Ile Cys Gly Arg Lys Phe Ala Arg Ser Asp Glu
         35                  40                  45 cgc aag cgt cat acc aaa atc cat aca agc atc atc gcg cgg gtg acg       192
Arg Lys Arg His Thr Lys Ile His Thr Ser Ile Ile Ala Arg Val Thr
     50                  55                  60 aag cgg gct ttg ctc gac gcc tta gcc att gag atg tta gat agg cac       240
Lys Arg Ala Leu Leu Asp Ala Leu Ala Ile Glu Met Leu Asp Arg His
 65                  70                  75                  80
```

```
cat act cac ttt tgc cct tta gaa ggg gaa agc tgg caa gat ttt tta        288
His Thr His Phe Cys Pro Leu Glu Gly Glu Ser Trp Gln Asp Phe Leu
                85                  90                  95 cgt aat aac gct agt ttt aga tgt gct tta cta agt cat cgc gat gga        336
Arg Asn Asn Ala Ser Phe Arg Cys Ala Leu Leu Ser His Arg Asp Gly
            100                 105                 110 gca aaa gta cat tta ggt aca cgg cct aca gaa aaa cag tat gaa act        384
Ala Lys Val His Leu Gly Thr Arg Pro Thr Glu Lys Gln Tyr Glu Thr
        115                 120                 125 ctc gaa aat caa tta gcc ttt tta tgc caa caa ggt ttt tca cta gag        432
Leu Glu Asn Gln Leu Ala Phe Leu Cys Gln Gln Gly Phe Ser Leu Glu
    130                 135                 140 aat gca tta tat gca ctc agc gct gtg ggg cat ttt act tta ggt tgc        480
Asn Ala Leu Tyr Ala Leu Ser Ala Val Gly His Phe Thr Leu Gly Cys
145                 150                 155                 160 gta ttg gaa gat caa gag cat caa gtc gct aaa gaa gaa agg gaa aca        528
Val Leu Glu Asp Gln Glu His Gln Val Ala Lys Glu Glu Arg Glu Thr
                165                 170                 175 cct act act gat agt atg ccg cca tta tta cga caa gct atc gaa tta        576
Pro Thr Thr Asp Ser Met Pro Pro Leu Leu Arg Gln Ala Ile Glu Leu
            180                 185                 190 ttt gat cac caa ggt gca gag cca gcc ttc tta ttc ggc ctt gaa ttg        624
Phe Asp His Gln Gly Ala Glu Pro Ala Phe Leu Phe Gly Leu Glu Leu
        195                 200                 205 atc ata tgc gga tta gaa aaa caa ctt aaa tgt gaa agt ggg tct aga        672
Ile Ile Cys Gly Leu Glu Lys Gln Leu Lys Cys Glu Ser Gly Ser Arg
    210                 215                 220 gac tag                                                                 678
Asp
225

<210> SEQ ID NO 2
<211> LENGTH: 225
<212> TYPE: PRT
<213> ORGANISM: Artificial Sequence
<220> FEATURE:
<223> OTHER INFORMATION: ZF-TetR-DD clone

<400> SEQUENCE: 2

Met Ala Ser Gly Pro Phe Gln Cys Arg Ile Cys Met Arg Asn Phe Ser
1               5                   10                  15

Arg Ser Asp His Leu Thr Thr His Ile Arg Thr His Thr Gly Glu Lys
                20                  25                  30

Pro Phe Ala Cys Asp Ile Cys Gly Arg Lys Phe Ala Arg Ser Asp Glu
            35                  40                  45

Arg Lys Arg His Thr Lys Ile His Thr Ser Ile Ile Ala Arg Val Thr
        50                  55                  60

Lys Arg Ala Leu Leu Asp Ala Leu Ala Ile Glu Met Leu Asp Arg His
65                  70                  75                  80

His Thr His Phe Cys Pro Leu Glu Gly Glu Ser Trp Gln Asp Phe Leu
                85                  90                  95

Arg Asn Asn Ala Ser Phe Arg Cys Ala Leu Leu Ser His Arg Asp Gly
            100                 105                 110

Ala Lys Val His Leu Gly Thr Arg Pro Thr Glu Lys Gln Tyr Glu Thr
        115                 120                 125

Leu Glu Asn Gln Leu Ala Phe Leu Cys Gln Gln Gly Phe Ser Leu Glu
    130                 135                 140

Asn Ala Leu Tyr Ala Leu Ser Ala Val Gly His Phe Thr Leu Gly Cys
145                 150                 155                 160
```

```
Val Leu Glu Asp Gln Glu His Gln Val Ala Lys Glu Arg Glu Thr
                165                 170                 175

Pro Thr Thr Asp Ser Met Pro Pro Leu Leu Arg Gln Ala Ile Glu Leu
            180                 185                 190

Phe Asp His Gln Gly Ala Glu Pro Ala Phe Leu Phe Gly Leu Glu Leu
        195                 200                 205

Ile Ile Cys Gly Leu Glu Lys Gln Leu Lys Cys Glu Ser Gly Ser Arg
    210                 215                 220

Asp
225
```

<210> SEQ ID NO 3
<211> LENGTH: 22
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 8-15
<223> OTHER INFORMATION: n = a, t, c, or g

<400> SEQUENCE: 3
cccacgcnnn nnnnngcgtg gg                                      22

<210> SEQ ID NO 4
<211> LENGTH: 7
<212> TYPE: PRT
<213> ORGANISM: Artificial Sequence
<220> FEATURE:
<223> OTHER INFORMATION: junction sequence

<400> SEQUENCE: 4

```
Arg Ala Ser Ile Met Arg Arg
 1               5
```

<210> SEQ ID NO 5
<211> LENGTH: 8
<212> TYPE: PRT
<213> ORGANISM: Artificial Sequence
<220> FEATURE:
<223> OTHER INFORMATION: junction sequence

<400> SEQUENCE: 5

```
Ser Val Arg Gly Arg Lys Val Pro
 1               5
```

<210> SEQ ID NO 6
<211> LENGTH: 7
<212> TYPE: PRT
<213> ORGANISM: Artificial Sequence
<220> FEATURE:
<223> OTHER INFORMATION: junction sequence

<400> SEQUENCE: 6

```
Arg Lys Val Asn Leu Val Pro
 1               5
```

<210> SEQ ID NO 7
<211> LENGTH: 7
<212> TYPE: PRT
<213> ORGANISM: Artificial Sequence
<220> FEATURE:
<223> OTHER INFORMATION: junction sequence
<220> FEATURE:

```
<221> NAME/KEY: VARIANT
<222> LOCATION: 1, 3, 6, 7
<223> OTHER INFORMATION: Xaa = any amino acid
<220> FEATURE:
<221> NAME/KEY: VARIANT
<222> LOCATION: 2
<223> OTHER INFORMATION: Xaa = Ile or Val
<220> FEATURE:
<221> NAME/KEY: VARIANT
<222> LOCATION: 4
<223> OTHER INFORMATION: Xaa = Gly or Ala

<400> SEQUENCE: 7

Xaa Xaa Xaa Xaa Arg Xaa Xaa
 1               5

<210> SEQ ID NO 8
<211> LENGTH: 7
<212> TYPE: DNA
<213> ORGANISM: Artificial Sequence
<220> FEATURE:
<223> OTHER INFORMATION: recognition sequence

<400> SEQUENCE: 8 cccacgc                                                                    7

<210> SEQ ID NO 9
<211> LENGTH: 7
<212> TYPE: DNA
<213> ORGANISM: Artificial Sequence
<220> FEATURE:
<223> OTHER INFORMATION: recognition sequence

<400> SEQUENCE: 9 gcgtggg                                                                    7

<210> SEQ ID NO 10
<211> LENGTH: 21
<212> TYPE: DNA
<213> ORGANISM: Artificial Sequence
<220> FEATURE:
<223> OTHER INFORMATION: syntheticaly generated oligonucleotide
<220> FEATURE:
<221> NAME/KEY: misc_feature
<222> LOCATION: 8-14
<223> OTHER INFORMATION: n = a, t, c, or g

<400> SEQUENCE: 10
cccacgcnnn nnnngcgtgg g                                                   21

<210> SEQ ID NO 11
<211> LENGTH: 7
<212> TYPE: PRT
<213> ORGANISM: Artificial Sequence
<220> FEATURE:
<223> OTHER INFORMATION: junction sequence

<400> SEQUENCE: 11

Ser Ile Ile Ala Arg Val Thr
 1               5

<210> SEQ ID NO 12
<211> LENGTH: 7
<212> TYPE: PRT
<213> ORGANISM: Artificial Sequence
<220> FEATURE:
<223> OTHER INFORMATION: junction sequence

<400> SEQUENCE: 12
```

```
Val Ile Thr Gly Arg Ala His
 1               5
```

<210> SEQ ID NO 13
<211> LENGTH: 7
<212> TYPE: PRT
<213> ORGANISM: Artificial Sequence
<220> FEATURE:
<223> OTHER INFORMATION: junction sequence

<400> SEQUENCE: 13

```
Val Val Ala Arg Thr Ala Gly
 1               5
```

<210> SEQ ID NO 14
<211> LENGTH: 7
<212> TYPE: PRT
<213> ORGANISM: Artificial Sequence
<220> FEATURE:
<223> OTHER INFORMATION: junction sequence

<400> SEQUENCE: 14

```
Val Val Thr Ala Arg Arg Gly
 1               5
```

<210> SEQ ID NO 15
<211> LENGTH: 7
<212> TYPE: PRT
<213> ORGANISM: Artificial Sequence
<220> FEATURE:
<223> OTHER INFORMATION: junction sequence

<400> SEQUENCE: 15

```
Arg Ile Val Gly Arg Ser Arg
 1               5
```

<210> SEQ ID NO 16
<211> LENGTH: 7
<212> TYPE: PRT
<213> ORGANISM: Artificial Sequence
<220> FEATURE:
<223> OTHER INFORMATION: junction sequence

<400> SEQUENCE: 16

```
Met Ile Lys Ala Arg Ser Gly
 1               5
```

<210> SEQ ID NO 17
<211> LENGTH: 7
<212> TYPE: PRT
<213> ORGANISM: Artificial Sequence
<220> FEATURE:
<223> OTHER INFORMATION: junction sequence

<400> SEQUENCE: 17

```
Arg Val Ile Ala Arg Ile Ser
 1               5
```

<210> SEQ ID NO 18
<211> LENGTH: 8
<212> TYPE: PRT
<213> ORGANISM: Artificial Sequence
<220> FEATURE:
<223> OTHER INFORMATION: junction sequence

<400> SEQUENCE: 18

```
Met Ile Val Gly Arg His Ile Val
 1               5
```

<210> SEQ ID NO 19
<211> LENGTH: 8
<212> TYPE: PRT
<213> ORGANISM: Artificial Sequence
<220> FEATURE:
<223> OTHER INFORMATION: junction sequence

<400> SEQUENCE: 19

```
Met Ile Arg Gly Arg Thr Lys Arg
 1               5
```

<210> SEQ ID NO 20
<211> LENGTH: 8
<212> TYPE: PRT
<213> ORGANISM: Artificial Sequence
<220> FEATURE:
<223> OTHER INFORMATION: junction sequence

<400> SEQUENCE: 20

```
Lys Val Val Gly Arg Ser Asn Gly
 1               5
```

<210> SEQ ID NO 21
<211> LENGTH: 8
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 1
<223> OTHER INFORMATION: Xaa = any amino acid,  e.g.,  Met, Ser, or Arg
<220> FEATURE:
<221> NAME/KEY: VARIANT
<222> LOCATION: 2
<223> OTHER INFORMATION: Xaa = Ile or Val
<220> FEATURE:
<221> NAME/KEY: VARIANT
<222> LOCATION: 3
<223> OTHER INFORMATION: Xaa = Thr, Val, Ile , Ala, Arg or Lys
<220> FEATURE:
<221> NAME/KEY: VARIANT
<222> LOCATION: 4
<223> OTHER INFORMATION: Xaa = Gly or Ala
<220> FEATURE:
<221> NAME/KEY: VARIANT
<222> LOCATION: 6
<223> OTHER INFORMATION: Xaa = any amino acid, e.g., Ser or Arg
<220> FEATURE:
<221> NAME/KEY: VARIANT
<222> LOCATION: 7
<223> OTHER INFORMATION: Xaa = any amino acid , e. g., Gly
<220> FEATURE:
<221> NAME/KEY: VARIANT
<222> LOCATION: 8
<223> OTHER INFORMATION: xaa = any amino acid

<400> SEQUENCE: 21

```
Xaa Xaa Xaa Xaa Arg Xaa Xaa Xaa
 1               5
```

ZINC FINGER-BASED DRUG-DEPENDENT GENE REGULATION SYSTEM

This application is a National Stage of International Application No. PCT/US02/39122, filed Dec. 9, 2002, which claims the benefit of priority from U.S. Provisional Application Ser. No. 60/338,407, filed Dec. 7, 2001.

TECHNICAL FIELD

This invention relates to the regulation of gene expression.

BACKGROUND

Proteins containing the eukaryotic $Cys_2His_2$ zinc finger DNA-binding motif are relatively flexible with respect to their sequence specificity (Wolfe et al., 2000, Ann. Rev. Biophys. Biomol. Struct. 29:183–212; Pabo et al., 2001, Ann. Rev. Biochem. 70:313–340). DNA recognition typically involves a tandem array of two or more zinc fingers. Fingers with a desired sequence specificity can be created by randomizing the residues involved in base-specific DNA recognition sequences and then selecting fingers with the desired specificity from the resulting library or by designing fingers based on understood principles of zinc finger-DNA recognition (Liu et al., J. Biol. Chem., 2002, 277(6):3850–6). For example, fingers with novel specificity have been selected using phage display (Rebar et al., 1996, Meth. Enzymol. 267:129–149) or using a bacterial two-hybrid system (Joung et al., 2000, Proc. Natl. Acad. Sci USA 97:7382–7387). Proteins with a desired sequence specificity are created by making an assembly of fingers that have been selected to have the desired sequence specificity.

Zinc finger proteins have been used successfully in vivo to alter gene expression by attaching repression or activation domains (Beerli et al., 2000, Proc. Natl. Acad. Sci. USA 97:1495–1500; Zhang et al., 2000, J. Biol. Chem. 275: 33850–3360; Liu et al., 2001, J. Biol. Chem. 276:11323–11334). Regulation of a gene by zinc fingers has also been made drug-dependent by using two types of accessory domains: 1) a zinc finger-homeodomain fusion protein wherein the association of an activation domain with this protein was rendered drug-dependent (Rivera et al., 1996, Nature Med. 2:1028–1032; Ye et al., 199, Science 283:88–91). This was accomplished by fusing protein domains to the activation and DNA-binding domains that could associate only in the presence of the drug rapamycin; and 2) a zinc finger-steriod receptor fusion protein that binds to DNA only in the presence of synthetic steroid receptor antagonists (Beerli et al., 2000, J. Biol. Chem. 275:32617–32627; Xu et al., 2001, Mol. Ther. 3:262–273).

The tetracycline receptor (TetR) is a component of the tetracycline resistance system (Tn10) in bacteria that represses expression of the tetracycline exporter pump (TetA) (Saenger, 2000, Angew Chem. Int. Ed. Engl. 39:2042–2052). This protein binds to an operator DNA sequence (tetO) as a homodimer in the absence of tetracycline (Tc), but in the presence of the drug it can no longer bind to DNA. Consequently transcription of TetA is no longer repressed. The structure of TetR bound to DNA containing the tetO sequence has been determined (Orth et al., 2000, Nat. Struct. Biol. 7:215–219), as has the structure of TetR with Tc bound (Hinrichs et al., 1994, Science 264:418–420). Examination of these structures suggests that an allosteric mechanism of inactivation of TetR occurs upon binding by Tc (Orth et al., 2000, Nat. Struct. Biol., 7:215–219). TetR is composed of two domains with different functions: the dimerization domain, which has at its core a four helix bundle, and the DNA-binding domains which folds into a helix-turn-helix (HTH) motif. These two domains are rigidly connected by an α-helix. Tc binds in a pocket in the dimerization domain of each monomer, and this results in a conformational change in the dimerization domain that translates down the connecting α-helix, and increases the distance between the helix-turn-helix motif of each monomer by about 3 Å. This is believed to be the reason that the TetR•Tc dimer can no longer bind to DNA containing the tetO sequence.

TetR has been used to form the basis for a drug-regulatable gene regulation system in eukaryotes (Williams et al., 2000, J. Appl. Physiol. 88:1119–1126). TetR is a bacterial protein and consequently, it should not interact with any of the components of the eukaryotic machinery. Moreover, most eukaryotic systems can tolerate Tc (or a similar derivative that binds to TetR) at high concentrations. A specific gene can be rendered drug-inducible simply by attaching a repression or activation domain to TetR, and introducing multiple copies of tetO in front of the gene of interest (Gossen et al., 1995, Science 268:1766–1769). This system has been further augmented by the creation of a modified TetR (rTetR) that cannot bind in the absence of tetracycline, but that binds the operator sequence (tetO) in the presence of the drug (Urlinger et al., 2000, Proc. Natl. Acad. Sci. USA 97:7963–1768). The primary limitation of this system is the necessity to introduce the tetO operator into the promoter of the gene of interest.

SUMMARY

The invention is based on the discovery that one can create a drug-regulated gene regulation system by creating a fusion polypeptide (chimera) that includes three portions: (i) a zinc finger (ZF) monomer, e.g., a Cys2His2 zinc finger protein, that recognizes a DNA sequence in the vicinity of the promoter of the gene to be targeted, (ii) a dimerization domain of a tetracycline repressor, which contains a drug-dependent switch, and (iii) an accessory domain to alter the expression of the target gene (such as an activation or repression domain). These chimeras are administered to, or expressed in, cells harboring the target genes to be regulated.

In general, the invention features a fusion polypeptide that regulates a target gene that includes a zinc finger monomer including an amino acid sequence that binds to a nucleic acid recognition sequence in the target gene; a dimerization domain of a tetracycline repressor linked to the zinc finger monomer such that the zinc finger can bind to the recognition sequence in the target gene; and an accessory domain that modulates a promoter operably linked with the target gene, wherein the accessory domain is linked to the zinc finger monomer such that the accessory domain is localized to the promoter when the zinc finger monomer binds to the recognition sequence.

In these polypeptides, the zinc finger monomer can include, for example, a portion of a Zif268 zinc finger, e.g., amino acids 333–416 of Zif268 (SEQ ID NO:23); or an amino acid sequence that binds to a TATA box; amino acids 498–560 of a *Drosophila* Tramtrak protein (SEQ ID NO:25); or amino acids 1 to 87 of artificial zinc finger protein MEY (SEQ ID NO:26). The dimerization domain can include, for example, amino acids 48–207 of an *E. coli* Tn10 Tet repressor (SEQ ID NO:28); amino acids 48–212 of a class E *E. coli* Tet repressor (SEQ ID NO:30); amino acids 48–218 of *E. Coli* Tet repressor RA1 (SEQ ID NO:31);

amino acids 48–216 of a Class A E. coli Tet repressor (SEQ ID NO:32); or amino acids 48–219 of a Class C E. Coli Tet repressor (SEQ ID NO:33).

The dimerization domain typically includes a pocket to which a drug like tetracycline (or a tetracycline analog such as anhydrotetracycline or doxycycline) binds to induce a conformational change of the fusion polypeptide that alters the ability of the zinc finger domain to bind to the recognition sequence. For example, binding of the drug, e.g., tetracycline, to the pocket in the dimerization domain may prevent the zinc finger monomer from binding to the recognition sequence, or binding of the drug to the pocket in the dimerization domain may enable the zinc finger monomer to bind to the recognition sequence.

In certain embodiments, the dimerization domain is linked to the zinc finger monomer by a junction sequence, e.g., a sequence of 4 to 12, e.g., 5 to 10, or 6 to 8 amino acids. For example, the junction sequence can be an amino acid sequence of seven amino acids having the sequence Xaa (Ile or Val) Xaa (Gly or Ala) Arg Xaa Xaa (SEQ ID NO:7), wherein Xaa is any amino acid. The junction can also include an additional amino acid or any type at the end of SEQ ID NO:7.

In using these fusion polypeptides, the zinc finger monomers are selected such that the recognition sequences are located in the vicinity of a promoter in the target gene, and two, there or more zinc finger monomers can be arranged in series in each fusion polypeptide. Further, the accessory domains can be a repression domain, e.g., a KRAB repression domain, or an activation domain, e.g., a VP16 activation domain.

In another aspect, the invention provides a nucleic acid molecule that includes a nucleic acid sequence that encodes one or more of the new fusion polypeptides. The nucleic acid molecule may be in a nucleic acid vector, which can be within a cell.

The invention also provides dimers, e.g., homodimers, which include two of the new fusion polypeptides. In use, the fusion polypeptides automatically form dimers in solution, e.g., in vivo.

In another aspect, the invention features methods of altering expression of a target gene in a cell by (a) providing a cell that contains the target gene; and (b) transfecting the cell with one or more nucleic acid molecules that encode one or more of the new fusion polypeptides; wherein expression of the fusion polypeptide alters expression of the target gene. In these methods, the target gene can be an endogenous or exogenous gene.

The methods can be controlled by adding a drug, such as tetracycline or an analog, to the cell in an amount effective to alter expression of the target gene. For example, addition of the drug can repress (inhibit) or activate (enhance) expression of the target gene. In other embodiments, the drug can be added, and thereafter removed tetracycline from the cell, e.g., at a specific time, to alter (repress or activate) expression of the target gene. In there methods, the nucleic acid molecule can be episomal in the cell or be integrated into genomic DNA of the cell. The cell can be in a subject, such as an animal or human patient.

In another aspect, the invention also features methods of regulating expression of a target gene in a subject by administering to the subject a fusion polypeptide in an amount effective to form sufficient dimers to bind to recognition sequences in the target gene, thereby regulating the expression of the target gene. A drug, such as tetracycline (or an analog), can be administered to the subject in an amount effective to alter expression of the target gene. Alternatively, the drug can be administered over time, e.g., by infusion, and thereafter administration of the drug can be ceased when the expression of the target gene is to be altered.

The invention also includes a transgenic non-human animal, such as a mouse, rabbit, pig, goat, fly, worm, or monkey, the nucleated cells of which include a transgene encoding a fusion polypeptide, wherein the animal exhibits induction or repression of a target gene in the presence (or absence) of tetracycline. In these animals, the target gene can be an endogenous or exogenous gene.

The term "nucleic acid molecule" includes DNA molecules (e.g., a cDNA or genomic DNA) and RNA molecules (e.g., an niRNA) and analogs of the DNA or RNA generated, e.g., by the use of nucleotide analogs. The nucleic acid molecule can be single-stranded or double-stranded.

The term "isolated" or "purified," when applied to a nucleic acid molecule, includes nucleic acid molecules that are separated from other materials, including other nucleic acids, which are present in the natural source of the nucleic acid molecule. For example, with respect to genomic DNA, the term "isolated" includes nucleic acid molecules that are separated from the chromosome with which the genomic DNA is naturally associated. Preferably, an "isolated" nucleic acid is free of sequences that naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that the preparation of a selected protein (e.g., ZF-TetR fusion polypeptide) has less than about 30%, (e.g., less than 20%, 10%, or 5%) by dry weight, of non-selected protein or of chemical precursors (e.g., a protein other than ZF-TetR polypeptide). Such a non-selected protein is also referred to herein as a "contaminating protein"). When the ZF-TetR polypeptide is recombinantly produced, it is also preferably substantially free of culture medium, i.e., culture medium represents less than about 20%, (e.g., less than about 10% or 5%) of the volume of the protein preparation. The invention includes isolated or purified preparations of at least 0.01, 0.1, 1.0, and 10 milligrams in dry weight.

"Misexpression or aberrant expression," as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject," as used herein, is an animal such as a mammal, e.g., an experimental animal such as a disease model, or a human. The subject can also be a non-human animal, e.g., a horse, cow, goat, or other domestic animal, or yeast, insects (e.g., *drosophila*), invertebrates (e.g., worms like *C. elegans*), reptiles, or fish.

A "purified preparation of cells," as used herein, refers to, in the case of plant or animal cells, an in vitro preparation of cells and not an entire intact plant or animal. In the case of cultured cells or microbial cells, it consists of a preparation of at least 10% a (e.g., about 20, 30, 40 or 50%) of the subject cells.

A promoter or other nucleic acid sequence is "operably linked" to a gene when it is connected with the gene such that the promoter can regulate expression of the gene. In certain embodiments, the promoter operably linked to a gene is located upstream of the gene in terms of the direction of transcription and translation.

An accessory domain is "localized" to a promoter when it is brought into sufficient proximity to the promoter so that it can induce an alteration in expression of the gene by inhibiting (repressing) or activating (enhancing) activity of the promoter.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is a representation of nucleic acid sequence that encodes a Zif268TetR fusion polypeptide (SEQ ID NO: 1), and the deduced amino acid sequence (SEQ ID NO:2).

FIG. 4A is a diagram of the mechanism of action of a "Tet-Off" polypeptide.

FIG. 4B is a diagram of the mechanism of action of a "Tet-On" polypeptide.

DETAILED DESCRIPTION

The invention relates to a drug-dependent, gene regulation system that combines the flexibility of zinc fingers, e.g., $Cys_2His_2$ zinc fingers, for DNA-binding specificity and the drug-regulatable properties of the tetracycline repressor dimerization domain. This new system is thus a tetracycline-inducible gene regulation system that has the advantages of the current Tet-ON and Tet-OFF systems, but that can also recognize any desired DNA sequence. This provides a method for external regulation of endogenous genes by inexpensive, bio-available, and well-tolerated drugs such as tetracycline or analogs. The fusion polypeptides and methods described herein are useful for investigating the effects of expression (or lack thereof) of a specific endogenous or exogenous nucleic acid sequence. For example, the technology greatly simplifies both the time and expense of creating "knockout" mice. In addition, because the system provides temporal control of gene expression, it bypasses the potential problem of embryonic lethality. Moreover, this system is also applicable to other model systems, facilitating the study of cancer-related genes in a variety of methodologies and settings.

General Methodology

In general, the system includes a fusion polypeptide or chimera that rigidly fuses the dimerization domain of the TetR, which provides a drug-dependent switch, to a zinc finger (ZF) domain, such as the zinc fingers of Zif268 (Elrod-Erickson, 1996, Structure, 4, 1171–1180), which provides target DNA specificity. An accessory domain that modulates a promoter operably linked to the target gene is typically attached to the N or C terminus of the zinc finger though a flexible linker. The accessory domain can be either an activation domain or a repression domain. Furthermore, the zinc finger and dimerization domains are typically linked via a junction sequence that is typically from 4 to 12 amino acids in length and that properly spaces the zinc finger domain from the dimerization domain. These polypeptide domains can be synthesized and linked, but are typically generated using standard recombinant genetic engineering techniques.

Figure 1A:
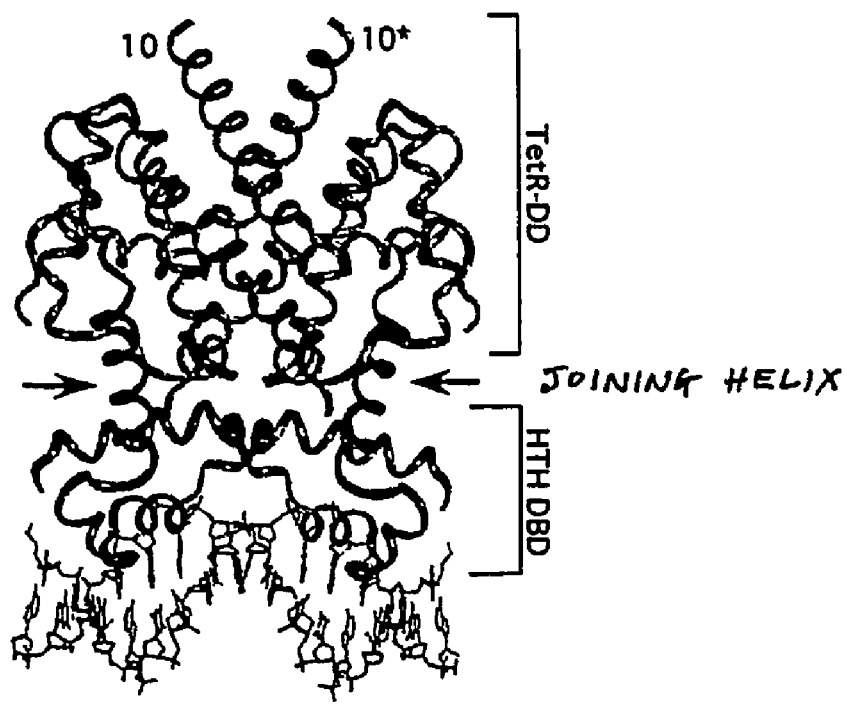
FIG. 1A is schematic three-dimensional representation of a naturally occurring tetracycline (Tet) repressor (Orth et al., 2000, Nat. Struct. Biol., 7:215–219).

A naturally occurring Tet repressor (TetR) is shown in FIG. 1A. The Tet repressor sequence used can be, for example, nucleotides 165–648 (encoding amino acids 48–207) of Genbank #X00694 (Class B, *E. coli* Tn10 tetR gene coding for tetR repressor) (SEQ ID NO:28); or nucleotides 226–722 (encoding amino acids 48–212) of Genbank #X14035 (Class E, *E. coli* tetR gene for class E Tet repressor (tetracycline resistance) (SEQ ID NO:30). Additional examples include amino acids 48–218 of Genbank #S07359 (Class D, *E. Coli* tetR gene RA1) (SEQ ID NO:31); or amino acids 48–216 of Genbank #RPECR1 (Class A, *E. Coli* tetR gene Tn1721) (SEQ ID NO:32); or amino acids 48–219 of Genbank #RPECYS (Class C, *E. Coli* tetR gene from pSC101) (SEQ ID NO:33).

Figure 1B:
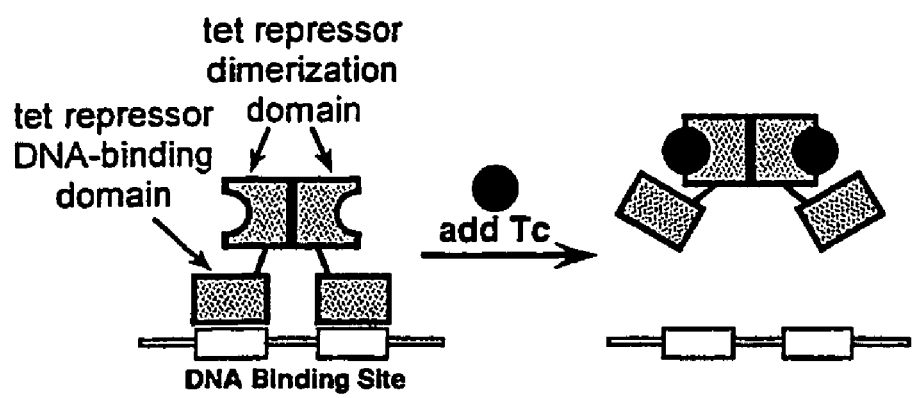
FIG. 1B is a diagram of the mechanism of action of the Tet repressor of FIG. 1A.

A diagram of the mechanism of action of these Tet repressors is shown in FIG. 1B. As shown in FIG. 1A, the TetR, which binds to DNA as a dimer, has two main domains, the TetR-dimerization domain (Tet-R-DD) and a helix-turn-helix DNA binding domain (HTH DBD), which are linked together by a "joining" helix (helix 4 at the arrow). The naturally occurring TetR is drug-dependent, in that it responds to tetracycline (Tc) or its analogs. As shown in FIG. 1B, when the TetR-DD binds to Tc, there is a conformational change in the dimerization domain (due to an allosteric mechanism) that propagates through the "joining" helix to the DNA binding domains. This results in an increase in the separation of the two DNA binding domains, thus preventing the dimer from binding to DNA that contains its target sequence.

The new fusion polypeptides (also referred to herein as constructs or chimeras) replace the helix-turn-helix DNA-binding motif of TetR with one or more zinc finger monomers, e.g., $Cys_2His_2$ zinc fingers. Examples of zinc finger sequences that can be used in the invention include Zif268 (egr1; Mus musculus early growth response 1 (Egr1), mRNA, Genbank accession NM_007913 (SEQ ID NO:22)), e.g., nucleotides 1291–1542, encoding amino acids 333–416 of Zif-268 (SEQ ID NO:23). Additional examples include zinc finger proteins selected to recognize the TATA box (Tatazf, clone #6 Genbank 1G2F_c, Wolfe et al., Structure, 2001, 9, 717–723); the *Drosophila* Tramtrak protein (Ttk, Genbank #X17121, amino acids 498–560) (SEQ ID NO:25; a designed zinc finger protein (MEY, Genbank #1MEYc, amino acids 1–87, Kim et al., J. M. Nat. Struct. Bio., 1996, 3(11) 940–945) (SEQ ID NO:26). Zinc fingers can also be selected or designed using standard techniques to recognize a specific recognition sequence in the target gene (for competitive binding inhibition of the gene) or in the vicinity of the target gene (to allow an accessory domain to localize to a promoter operably linked to the target gene), and then incorporated into this construct. Thus, the invention provides great flexibility in selecting target genes to be regulated.

Figure 2A:
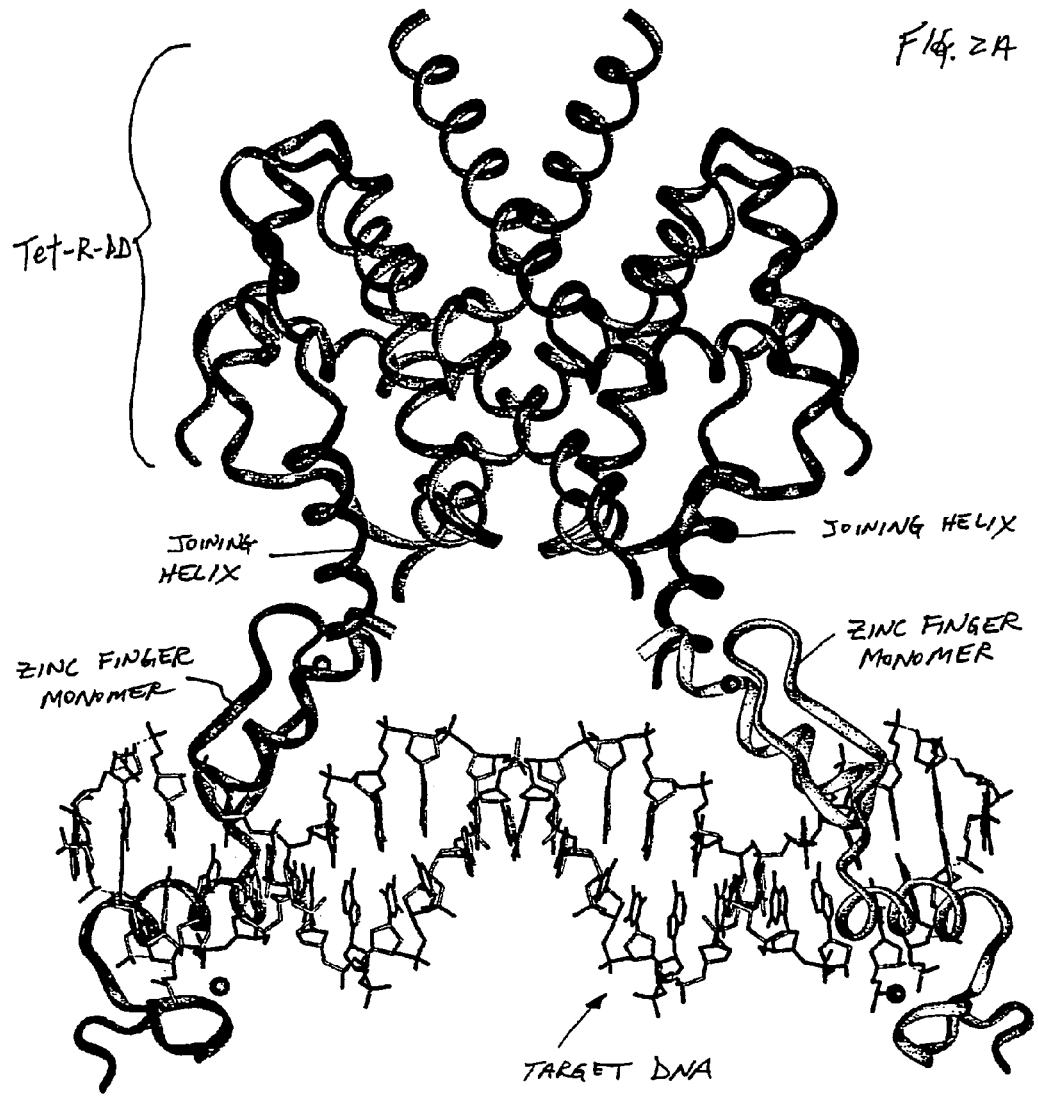
FIG. 2A is a schematic representation of a model of a Zif268TetR fusion polypeptide dimer.
Figure 2B:
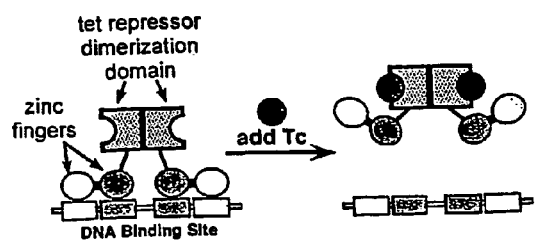
FIG. 2B is a diagram of the mechanism of action of the dimer of FIG. 2A.

As shown in FIG. 2A, the chimera comprises a fusion of zinc fingers to the TetR-DD at the "joining" helix, and DNA recognition occurs when the fusion polypeptides form dimers. Also shown is a target DNA strand (the target gene), to which the zinc fingers bind. In some embodiments, the dimerization domain, which promotes homodimerization, is also modified. In such embodiments, a modified version of the Tet repressor dimerization element is used that forms obligate heterodimers. There are seven related classes of Tet repressor, and although they are highly related, some classes, such as B and E, do not appreciably form heterodimers. Based on the structural information that exists (see, e.g., Orth et al., Nat. Struct. Biol., 7, 215–9 (2000) and Hinrichs. et al., Science, 264, 418–20 (1994)) and the sequences of these classes, hybrid dimerization domains are made that preferentially heterodimerize by combining specificity determinants from the different classes. These designs will be based on a "knobs-in-holes" approach to enforce heterodimeric specificity (see, e.g., Clemons et al., Chem. Biol., 9, 49–61, 2002).

The accessory domain is shown, e.g., in FIGS. 4A and 4B (VP16 activator in this figure), and is linked to the N or C terminus of the zinc finger monomer(s) by a flexible spacer. The accessory domain can be an activation domain or a repression domain. Examples of activators include the VP16 activation domain and the p65 activation domain. Examples of repression domains include the KRAB repression domain (for mammalian systems), the repression domain from Groucho for flies, or the Sin3 or Ssn6 co-repressors. This accessory domain can be part of the fusion polypeptide, or can be synthesized and then attached to the zinc finger of the fusion polypeptide.

The zinc finger monomer(s) and the dimerization domain can be linked by a junction sequence of about 4 to 12, e.g., 5 to 10, or 6 to 8 amino acids that properly space the zinc finger monomer(s) from the dimerization domain. For example, the junction sequence can have seven or eight amino acids as shown in Table 1 below. This set of junction sequences was developed by creating clones expressing fusion polypeptides selected to bind to recognition sites in target genes separated by an 8 base pair gap between the recognition sites (half sites) recognized by the zinc fingers.

TABLE 1

| Clone # | Junction Position | | | | | | | | |
|---|---|---|---|---|---|---|---|---|---|
| | 1 | 2 | 3 | 4 | 5 | 6 | 7 | 8 | |
| j | V | I | T | G | R | A | H | — | (SEQ ID NO:12) |
| f | V | V | A | R | T | A | G | — | (SEQ ID NO:13) |
| c | V | V | T | A | R | R | G | — | (SEQ ID NO:14) |
| a | R | I | V | G | R | S | R | — | (SEQ ID NO:15) |
| E1 | M | I | K | A | R | S | G | — | (SEQ ID NO:16) |
| F1 | S | V | R | G | R | K | V | P | (SEQ ID NO:5) |
| G1 | R | V | I | A | R | I | S | — | (SEQ ID NO:17) |
| H1 | M | I | V | G | R | H | I | V | (SEQ ID NO:18) |
| I1 | M | I | R | G | R | T | K | R | (SEQ ID NO:19) |
| A/D | S | I | I | A | R | V | T | — | (SEQ ID NO:11) |
| B | K | V | V | G | R | S | N | G | (SEQ ID NO:20) |
| consensus: | any | i/v | t/v/+ | g/a | R | any | any | any | (SEQ ID NO:21) |

Based on the sequences in this table, the junction sequence can have 7 amino acids that have the sequence Xaa (Ile or Val) Xaa (Gly or Ala) Arg Xaa Xaa (SEQ ID NO:7), wherein Xaa is any amino acid. For example, the sequence can be SIIARVT (SEQ ID NO:11). An additional amino acid(s) can be added at either end of this consensus sequence. The amino acid at position 1 can be, e.g., M, S, or R. The amino acid at position 2 can be Ile. The amino acid at position 3, can be, for example, T, V, I, A, R, or K. The amino acid at position 6 can be, e.g., S or R. The amino acid at position 7 can be, e.g., G.

Figure 5:
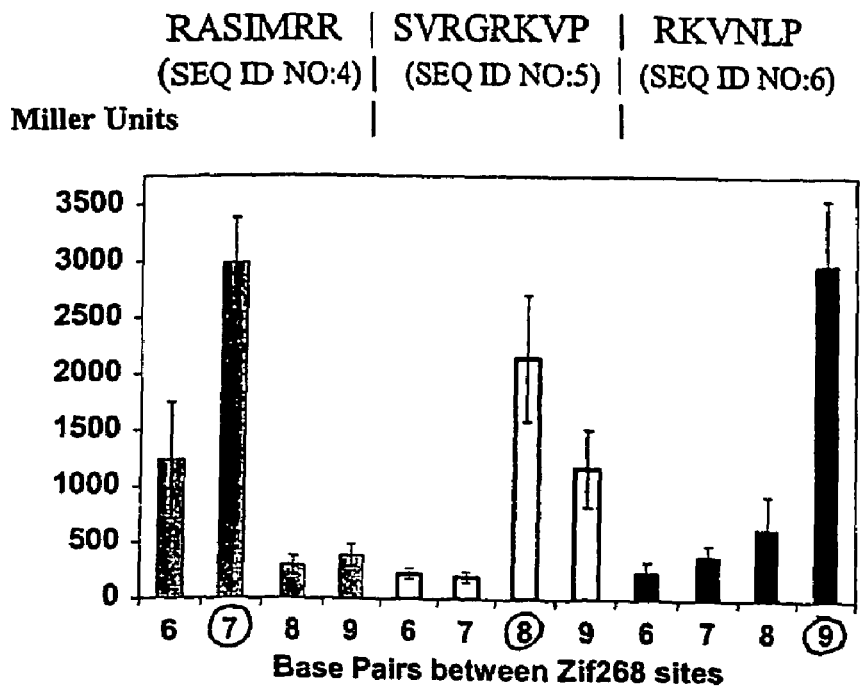
FIG. 5 is a bar graph that illustrates the activation of four different LacZ reporters by selected ZF-TetR clones. The four LacZ reporters have 6, 7, 8 or 9 base pairs between the Zif268 binding sites.

As shown in FIG. 5, other sequences of the junction sequence can be RASIMRR (SEQ ID NO:4), SVRGRKVP (SEQ ID NO:5), or RKVNLVP (SEQ ID NO:6).

FIG. 3 shows the nucleic acid sequence (SEQ ID NO:1) that encodes the reselected zinc finger construct that was selected to recognize Zif268 binding sites that are separated by an 8 base pair gap, and its amino acid sequence (SEQ ID NO:2). The amino acids in bold are the seven amino acids in the junction sequence between the zinc fingers and the TetR-DD that were randomized in the selections.

The new chimeras are created in two stages. First, using structure-based design, a fusion point for the TetR dimerization domain (TetR-DD) and the zinc fingers, e.g., finger 3 of Zif268, is chosen. Based on this analysis, prototypes are created and tested for their ability to recognize a palidromic sequence containing the DNA recognition sequences (half-sites) for the fingers of the zinc finger, e.g., Zif268, with different numbers of intervening base pairs. The appropriate spacing of the half-sites will depend on the precise geometry of the ZnF-TetR-DD dimer, which cannot be defined with absolute certainty based on the computer modeling. Consequently, a number of different intervening base pair sequence lengths between the half-sites were examined (6, 7, 8, and 9 base pairs). The prototypes are assayed, e.g., for their ability to activate LacZ expression in a bacterial two-hybrid system (Joung et al., supra), which provides a simple in vivo assay for the ability of a DNA-binding protein to find a target sequence in the context of genomic DNA (a large amount of non-specific DNA). Prototypes that are able to activate LacZ expression in such a system can be further optimized for sequence-specific DNA recognition and drug dependent binding, e.g., using phage display or a bacterial two-hybrid system.

Libraries of chimeras are created by randomizing the amino acids in the junction between the zinc fingers and the TetR-DD, while also varying the number of residues within the junction to allow selection of an optimal spacer length, which will rigidify the junction between these two domains. These libraries are displayed as homodimers, e.g., on the gene III coat proteins of filamentous (fd) phage. Selections are done using standard "bio-panning" procedures (see, e.g., Rebar et al., Meth. Enzymol., 267, 129–149, 1996), e.g., binding phage to the solid-support bound target site, washing extensively, and then eluting the desired phage by adding Tc to the solution, to select for chimeras that are inactivated by the presence of the drug. This permits the selection of chimeras, e.g., ZF-TetR-DD chimeras, which can recognize the target DNA sequence only in the absence of Tc (see FIG. 4A, "Tet-Off"; ZiftetR$^{OFF}$).

Chimeras that bind to a specific target DNA only in the presence of Tc (e.g., Zif268-TetR$^{ON}$, are selected by binding the libraries to their target sites in the presence of Tc, washing extensively in the presence of Tc, and then eluting the desired phage by removing Tc from the solution. This allows the selection of chimeras that can bind to target DNA only in the presence of Tc (see FIG. 4B, "Tet-On").

In some embodiments, some or all of the mutations in the TetR-DD that give the rTetR phenotype are included. In other embodiments, mutations in the TetR-DD are randomized using mutagenic PCR or using DNA shuffling methods between related TetR-DD genes (Stemmer, Nature, 1994, 370(6488):389–91) to achieve the desired phenotype. ZF-TetR-DD chimeras with novel DNA binding specificity are made by incorporating zinc fingers with different DNA-binding specificity into this system.

Mutations can be made in the Tet repressor dimerization domain, e.g., to result in a reverse phenotype, such that the tetR binds to DNA only in the absence of Tc as described in Gossen et al., Science, 1995, 268 1766–1769 and Urlinger et al., Proc. Natl. Acad. Sci., USA, 97, 7963–8 (2000). A yeast-based replica plating system can also be used to display the Zif268-TetR constructs (see, e.g., Urlinger et al., Proc. Natl. Acad. Sci., USA, 97, 7963–8, 2000). The size of the libraries that can be searched using this yeast-based system are much smaller than phage display or the bacterial two-hybrid system ($\sim 10^5$ verses $\sim 10^{10}$).

DNA-Binding Domain and the Dimerization Domain of TetR

The ability to create a chimera having a rigid fusion has been demonstrated by creating a zinc finger-leucine zipper fusion protein that binds DNA as a dimer (Wolfe et al., 2000, Structure 8:739–750). This was done in two stages. First, structure-based design, which involves using the DNA-bound structures of protein and computer modeling, was used to design a prototype (e.g., as described in Pomerantz et al., 1995, Science 267:93–96; and Pomerantz, 1998, Biochemistry 37:965–70). Using this approach, a prototype was created and then optimized using phage display by randomizing the junction between the zinc finger and leucine zipper domains and varying the number of residues in this junction. From this library, a dimeric protein with a high degree of sequence specificity was obtained.

Figure 7:
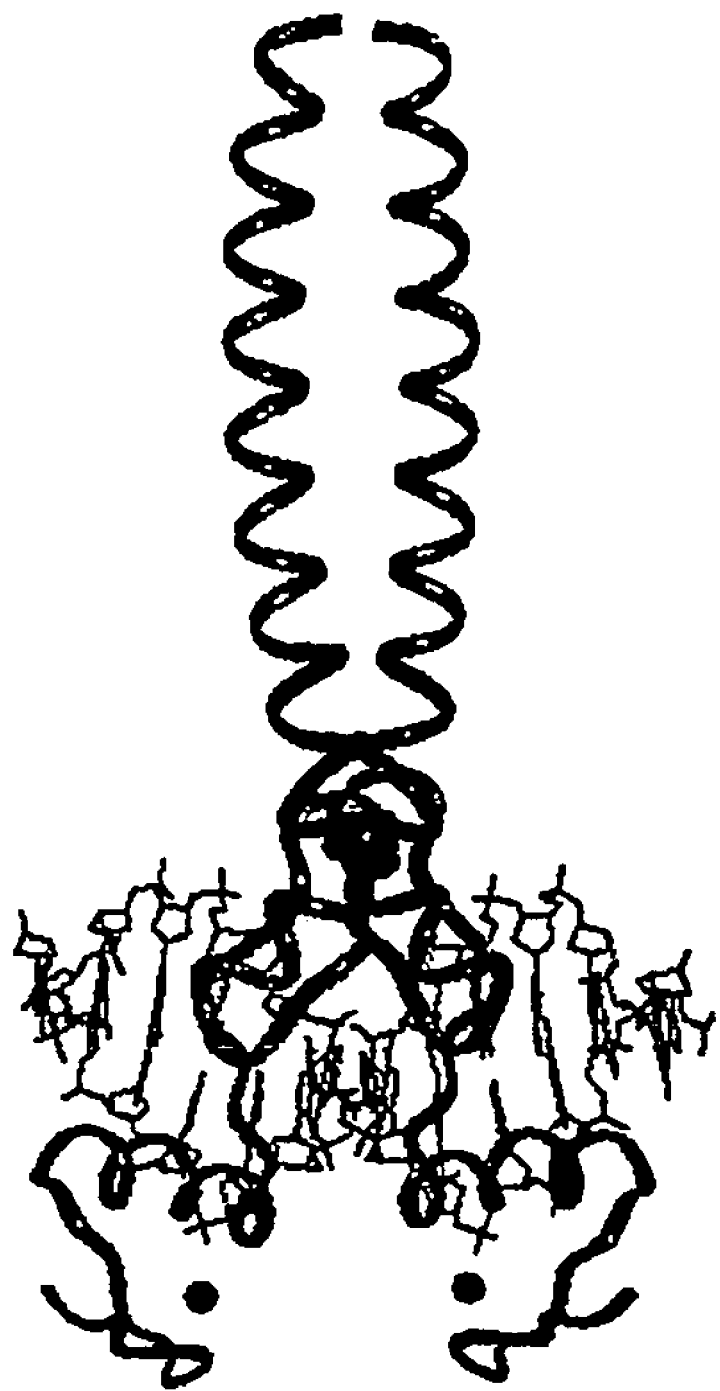
FIG. 7 is schematic three-dimensional representation of a zinc finger—leucine zipper fusion polypeptide dimer.

The structure of the dimeric zinc finger—leucine zipper fusion polypeptide was solved using X-ray crystallography to 1.5 Å resolution (FIG. 7). This structure demonstrates that the selected junction sequence is not disordered, as would occur with the use of a flexible linker that was employed in previous structure-based design approaches. Instead the selected junction sequence has created a rigid fusion of these domains, which rigidifies the interface. This type of rigidification of a junction between two different domains is important to the successful construction of a ZnF-TetR-DD chimera, which relies on a conformational change for its drug-dependent behavior.

Creation of a Tc-dependent DNA-Binding Domain that Utilizes Zinc Fingers for Sequence-Specific DNA Recognition Previous Tc-dependent gene regulation has used TetR, which recognizes tetO, or a modified version of TetR that recognizes a tetO sequence with a single base pair substitution in each half-site. The incorporation of zinc fingers for DNA-recognition allows essentially any given sequence to be recognized. This creates a system that is more flexible than the known TetR system, because it does not require installation of the tetO sequence before the target gene to be regulated. Instead, the zinc fingers in the context of the TetR-DD can be tailored to recognize a segment of the DNA in the vicinity of the promoter of the target gene. This will allow an appended accessory domain, such as an activation or repression domain, to alter the expression level of the endogenous gene. Multiple methods have been described that allow zinc fingers to be selected or designed to recognize different DNA sequences. This attribute of the new chimeric constructs represents an important fundamental improvement.

In the past, when genes were placed under tetR control in transgenic mice or other model systems, it was necessary not only to introduce a transgene into the genome that contained the tetO sequence upstream of the gene of interest, but also to introduce the tetR construct as well. On the other hand, the new drug-dependant gene regulation system can be used to easily control expression of an endogenous target gene without the need for any other construct. Due to size constraints on the length of DNA that can be incorporated into a transgenic animal, a transgene usually consists of is a single cDNA construct, and consequently it represents only one potential alternately splice variant of that gene. In higher organisms the majority of genes have multiple isoforms that can be created by alternate splicing, and many of these isoforms, not just a single variant, may be crucial to the biological function of this protein.

For instance, single isoforms of VEGF have been examined in mice, and when they are overexpressed they encourage vascularization of surrounding tissues, but this new vasculature is leaky (Detmar et al., 1998, J. Invest. Dermatol. 111:1–6; Larcher et al., 1998, Oncogene 17:303–311; Thurston et al., 1999, Science 286:2511–2514). A study in which a master regulator of the VEGF gene (Hif-1α) was used to increase expression from the native gene resulted in an increase in all of the isoforms of VEGF, and an increase in normal vacularization (Elson et al., 2001, Genes Dev. 15:2520–2532). The new ZF-TetR-DD system allows the effects of the entire population of protein isoforms to be examined in the appropriate stoichiometry because it activates (or represses, depending on the type of accessory domain) the endogenous gene instead of a transgene. Because the endogenous gene contains the natural intron-exon structure, the resulting RNA produced by transcription will be spliced in a tissue-specific manner to provide all of the naturally occurring splice variants.

In Vivo DNA Binding Specificity and Efficacy

Studies of other drug-based zinc finger DNA recognition systems have demonstrated that these systems can be effective in cell culture assays, or when expressed by transgenes in mice (see, e.g., Rebar et al., Nat. Med., 2002; 8(12): 1427–32). However their specificity with respect to gene regulation is not known. The specificity requirements for targeting a single gene in vivo, with regards to the length of the sequence that needs to be targeted and the appropriate affinity of the DNA-binding domain, can be determined by transcriptional profiling using DNA microarrays. The exact requirements for unique addressing with a genome are not known, but for example, recognizing a unique DNA sequence in the human genome requires, on average, a site containing 16 or more base pairs. The new chimeras use two separate sets of zinc fingers in the context of a dimer to recognize an extended target sequence. The DNA-binding specificity of the new chimeras will be enhanced by selecting the junction between the zinc fingers and the TetR-DD to allow binding to only one specific intervening spacing (e.g., of 8 base pairs) of the half-sites recognized by the zinc fingers in each monomer. This overcomes the problem that flexible linkers sometimes do not adequately constrain neighboring DNA-binding domains such that they can bind in many different registers on the DNA. The effectiveness of this approach has been demonstrated in the Zif268-GCN4 chimera described in Wolfe et al., Structure, 8, 739–750 (2000). This protein has a strong preference for only one spacing of the half sites, and the DNA-binding domains are constrained to bind in a single unique orientation.

The other potential solution to recognizing a single target site in a genome (and thus altering the expression of only a single gene) is to create a single, longer array of zinc fingers (e.g., 3, 4, 5, 6 or more arranged in series in a tandem array) for DNA recognition. This has been done with a single-chain variant of the steroid receptor domain (Beerli et al., J. Biol. Chem., 275, 32617–27 (2000)). However, dimerization provides a superior solution to this problem because the zinc fingers are broken into two component parts, which will provide potential advantages for DNA recognition and equilibration if the system functions cooperatively.

Tetracycline has Well-Defined Pharmacokinetic Properties and Few Side Effects

Tetracycline and its derivatives and analogs are generally well tolerated by eukaryotic systems whereas compounds used in the other drug-based systems have undesirable side effects on eukaryotic cellular processes. For example, rapamycin is a immunosuppressant (Abraham, R. T. & Wiederrecht, G. J. Ann. Rev. Immunol., 14, 483–510 (1996)), and steroid analogs such as 4-hydroxytamoxifen are known to affect the function of certain steroid receptors (Coward et al., Proc. Natl. Acad. Sci. U S A, 98, 8880–4 (2001)). Consequently, if a choice of all of the drugs previously mentioned were available for a drug-based gene therapy system, Tc would be the drug, of choice.

Recombinant Expression Vectors, Host Cells, and Genetically Engineered Cells

The invention includes vectors, preferably expression vectors, which contain a nucleic acid that encoded the chimeras described herein. As used herein, the term "vector" refers to a nucleic acid molecule capable of transporting another nucleic acid to which it has been linked and can include a plasmid, cosmid, or viral vector. The vector can autonomously replicate or it can integrate into a host DNA. Viral vectors include, e.g., replication-defective retroviruses, adenoviruses and adeno-associated viruses.

Two different cDNAs are required to encode the two fusion polypeptides of a single heterodimer or homodimer, but these can be introduced as a single transgene with one promoter, and an internal ribosome entry site separating the two genes. This allows both chimeric polypeptides to be translated from a single mRNA. FIG. 3 contains a selected ZF-TetR-DD clone (nucleic acid sequence (SEQ ID NO:1) and deduced amino acid sequence (SEQ ID NO:2)) that binds to DNA as a dimer. Each monomer contains a set of zinc fingers (in this case amino acids 1–57 derived from fingers 2 and 3 of Zif268 (SEQ ID NO:23)), a selected junction sequence linker (amino acids 58–64) and the tetR-DD (amino acids 65–226 from the class B tetR gene (SEQ ID NO:28)). This particular clone binds to a pair of recognition sequences in a target gene that has two zif268 binding sites separated by 8 base pairs (5'-CCCACGCNNNNNNNNGCGTGGG-3' (SEQ ID NO:3), where N is any DNA base).

Thus, one zinc finger monomer in the dimer binds to the nucleic acid recognition sequence CCCACGC (SEQ ID NO:8), and the other binds to the recognition sequence GCGTGGG (SEQ ID NO:9), which is the inverse complementary sequence of SEQ ID NO:8. Such pairs of recognition sequences separated by a specific number of base pairs (e.g., 7, 8, or 9), can be found in a variety of endogenous genes, and specific zinc fingers can be designed using standard techniques to bind to these pairs of recognition sequences (half-sites) when the zinc fingers are paired in a dimer.

A vector can include a ZF-TetR nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce ZF-TetR polypeptides encoded by nucleic acids as described herein.

The recombinant expression vectors of the invention can be designed for expression of ZF-TetR polypeptides in prokaryotic or eukaryotic cells. For example, polypeptides of the invention can be expressed in E. coli, insect cells (e.g., using baculovirus expression vectors), yeast cells, or mammalian cells (e.g., CHO or COS cells). Suitable host cells are discussed further in Goeddel, (1990) Gene Expression Technology: Methods in Enzymology 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene, 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

One can maximize recombinant protein expression in E. coli by expressing the protein in a host bacteria with an impaired capacity to proteolytically cleave the recombinant protein (Gottesman, S., (1990) Gene Expression Technology: Methods in Enzymology, 185, Academic Press, San Diego, Calif. 119–128). Another strategy is to alter the nucleic acid sequence of the nucleic acid to be inserted into an expression vector so that the individual codons for each amino acid are those preferentially utilized in E. coli (Wada et al., (1992) Nucleic Acids Res., 20:2111–2118). Such alteration of nucleic acid sequences of the invention can be carried out by standard DNA synthesis techniques.

When used in mammalian cells, the expression vector's control functions are often provided by viral regulatory elements. For example, commonly used promoters are derived from polyoma, Adenovirus 2, cytomegalovirus and Simian Virus 40.

In certain embodiments, a recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987), Genes Dev. 1:268–277), lymphoid-specific promoters (Calame and Eaton (1988)Adv. Immunol., 43:235–275), promoters of T cell receptors (Winoto and Baltimore (1989) EMBO J., 8:729–733) and immunoglobulins (Banerji et al. (1983) Cell, 33:729–740; Queen and Baltimore (1983) Cell, 33:741–748), neuron-specific promoters (e.g., the neurofilament promoter; Byrne and Ruddle (1989) Proc. Natl. Acad. Sci., USA, 86:5473–5477), pancreas-specific promoters (Edlund et al. (1985) Science, 230:912–916), and mammary gland-specific promoters (e.g., milk whey promoter; U.S. Pat. No. 4,873,316 and European Application Publication No. 264,166). Developmentally-regulated promoters can also be used, for example, the murine hox promoters (Kessel and Gruss (1990) Science, 249:374–379) and the α-fetoprotein promoter (Campes and Tilghman (1989) Genes Dev., 3:537–546).

Another aspect the invention provides a host cell that includes a nucleic acid molecule described herein, e.g., a ZF-TetR nucleic acid molecule, within a recombinant expression vector or a ZF-TetR nucleic acid molecule containing sequences that allow it to insert into the host cell's genome as a transgene. This can be accomplished with high efficiency using a lentiviral vector such as described in Lois et al., Science, 2002, 295(5556):868–72. The terms "host cell" and "recombinant host cell" are used interchangeably herein. Such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can-be used to produce (i.e., express) a ZF-TetR protein, e.g., for structural analysis. Accordingly, the invention further provides methods for producing a ZF-TetR protein using host cells as described herein. In one embodiment, the method includes culturing a host cell (into which a recombinant expression vector encoding a ZF-TetR protein has been introduced) in a suitable medium such that a ZF-TetR protein is produced. The method can further include isolating a ZF-TetR protein from the medium or the host cell.

In another aspect, the invention features, a cell or purified preparation of cells that include a ZF-TetR transgene. The cell preparation can consist of human or non-human cells, e.g., rodent cells such as mouse or rat cells, rabbit cells, or pig or goat cells. In preferred embodiments, the cell or cells include a ZF-TetR transgene. The ZF-TetR transgene can be one that is induced or repressed in the presence of tetracycline.

In another aspect, the invention features a human cell, e.g., a cultured human cell, transformed with nucleic acid, which encodes a subject ZF-TetR polypeptide.

Functional Gene Knockouts with Temporal Control and other Transgenic Animals

The new chimeras and nucleic acids can be used to create functional gene knockout animals as well as other types of transgenic animals. Such animals are useful for studying the function and/or activity of a ZF-TetR protein, or for studying the function of a specific gene in an organism by noting the phenotype that results when the gene is knocked-out at a certain time, e.g., at a specific stages of development. This temporal feature is useful, e.g., for studying embryonic lethal genes. The ZF-TetR-DD system provides full temporal control, permitting a native gene to be induced/repressed repeatedly. Other uses include ascertaining how a particular gene is involved in the development of a specific disease, by examining how the presence, absence, or overexpression of a gene (note: all of the relevant splice variants will be present) affects the progression or development of a disease, such as cancer.

A "transgenic animal or organism" is a non-human animal or organism, preferably a mammal, e.g., a rodent such as a rat or mouse, in which one or more of the cells of the animal (e.g., both the somatic and/or germ cells), includes a transgene. Other examples of transgenic animals include non-human primates, sheep, dogs, cows, goats, chickens, amphibians, insects such as *Drosophilia*, and worms such as *C. elegans*. This system can also be used in plants and yeast. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes. Thus, a transgenic animal can be one in which expression of an endogenous gene or an exogenous gene is altered by expression of a ZF-TetR gene that was introduced as an exogenous DNA molecule into a cell of the animal or an ancestor (e.g., when the gene is introduced into the germ line) of the animal, e.g., an embryonic cell of the animal, prior to development of the animal.

Traditionally, gene knockout animals, such as knockout mice, are created by interrupting a single allele of the gene of interest in embryonic stem (ES) cells, creating chimeric animals using these ES cells, and then creating F1 progeny from the chimera (see, e.g., Williams et al., 2000, J. Appl. Physiol., 88:1119–1126). Using the ZF-TetR-DD system, repression of both alleles of a gene is accomplished by tailoring the zinc fingers in this drug-regulatable system to recognize a target sequence in the promoter of the gene of interest, and attaching a repression domain such as a KRAB repression domain (for mammalian systems), the repression domain from Groucho for flies, or the Sin3 or Ssn6 co-repressors. A transgenic animal, e.g., mouse, that expresses this construct requires only the non-specific integration of a single construct, and thus provides a more efficient method for creating a functional "knockout" mouse that is "knocked out" on command by the addition of Tc.

In general, to construct a transgenic animal expressing a desired gene, one creates a transgene construct that includes the desired promoter (which could be tissue-specific) and the coding sequence of the gene of interest (in this case the two ZF-tetR-DD monomers encoded in a single cDNA transcript with an internal ribosome entry site separating the two genes). This transgene is injected into a fertilized oocyte, which is implanted in a pseudo-pregnant female. Multiple oocytes are implanted so that a number of F1 progeny are produced. The F1 progeny are then tested for the expression level of the construct, and the tissue-specific nature of expression. The F1 progeny with the desired expression pattern/level can be used as the founder for the animal colony.

There are various methods for generating transgenic animals. One method is by microinjection of a gene construct into the pronucleus of an early stage embryo (e.g., before the four-cell stage; Wagner et al., 1981, Proc. Natl. Acad. Sci., USA, 78:5016; Brinster et al., 1985, Proc. Natl. Acad. Sci., USA, 82:4438). Alternatively, the transgene can be introduced into the pronucleus by retroviral infection. A detailed procedure for producing such transgenic mice has been described (see e.g., Hogan et al., Manipulating the Mouse Embryo, Cold Spring Harbour Laboratory, Cold Spring Harbour, N.Y. (1986); U.S. Pat. No. 5,175,383 (1992)). This procedure has also been adapted for other animal species (e.g., Hammer et al., Nature 315:680 (1985); Murray et al., Reprod. Fert. Devl. 1:147 (1989); Pursel et al., Vet. Immunol. Histopath. 17:303 (1987); Rexroad et al., J. Reprod. Fert. 41 (suppl):119 (1990); Rexroad et al., Molec. Reprod. Devl. 1:164 (1989); Simons et al., BioTechnology 6:179 (1988); Vize et al., J. Cell. Sci. 90:295 (1988); and Wagner, J. Cell. Biochem. 13B (suppl):164 (1989)).

In brief, the procedure involves introducing the transgene into an animal by microinjecting the construct into the pronuclei of the fertilized mammalian egg(s) to cause one or more copies of the transgene to be retained in the cells of the developing mammal(s). Following introduction of the transgene construct into the fertilized egg, the egg may be incubated in vitro for varying amounts of time, or reimplanted a surrogate host, or both. One common method is to incubate the embryos in vitro for about 1–7 days, depending on the species, and then reimplant them into the surrogate host. The presence of the transgene in the progeny of the transgenically manipulated embryos can be tested by Southern blot analysis of a segment of tissue.

Another method for producing germ-line transgenic animals is through the use of embryonic stem (ES) cells. The gene construct can be introduced into ES cells by homologous recombination (Thomas et al., Cell, 51:503 (1987); Capecchi, Science, 244:1288 (1989); Joyner et al., Nature, 338:153 (1989)) in a transcriptionally active region of the genome. A suitable construct can also be introduced into ES cells by DNA-mediated transfection, such as by electroporation (Ausubel et al., Current Protocols in Molecular Biology, John Wiley & Sons (1987)). Detailed procedures for culturing embryonic stem cells (e.g., ES-D3, ATCC# CCL-1934, ES-E14TG2a, ATCC# CCL-1821, American Type Culture Collection, Rockville, Md.) and methods of making transgenic animals from embryonic stem cells can be found in Teratocarcinomas and Embryonic Stem Cells, A Practical Approach, ed. E. J. Robertson (IRL Press, 1987). In brief, the ES cells are obtained from pre-implantation embryos cultured iii vitro (Evans, M. J., et al., 1981, Nature, 292: 154–156). Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal.

In the above methods, the transgenic construct can be introduced as a linear construct, a circular plasmid, or a viral vector, which can be incorporated and inherited as a transgene integrated into the host genome. The transgene can also be constructed so as to permit it to be inherited as an extrachromosomal plasmid (Gassmann, M. et al., 1995, Proc. Natl. Acad. Sci. USA 92:1292). A plasmid is a DNA molecule that can replicate autonomously in a host.

The transgenic, non-human animals can also be obtained by infecting new cells either in vivo (e.g., direct injection), ex vivo (e.g., infecting the cells outside the host and later reimplanting), or in vitro (e.g., infecting the cells outside host) with a recombinant viral vector carrying the gene encoding the ZF-TetR-DD chimera Examples of suitable viral vectors include recombinant retroviral vectors (Valerio et al., 1989, Gene, 84:419; Scharfman et al., 1991, Proc. Natl. Acad. Sci., USA, 88:462; Miller, D. G. & Buttimore, C., 1986, Mol. Cell. Biol., 6:2895), recombinant adenoviral vectors (Freidman et al., 1986, Mol. Cell. Biol., 6:3791; Levrero et al., 1991, Gene, 101:195), and recombinant Herpes simplex viral vectors (Fink et al., 1992, Human Gene Therapy, 3:11). Recombinant retroviral vectors capable of transducing and expressing structural genes (e.g., ZF-TetR genes) inserted into the genome of a cell are produced by transfecting the recombinant retroviral genome into suitable packaging cell lines such as PA317 and Psi-CRIP (Cornette et al., 1991, Human Gene Therapy 2:5–10; Cone et al., 1984, Proc. Natl. Acad. Sci., USA, 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166: 769), and also have the distinct advantage of not requiring mitotically active cells for infection.

Clones of the non-human transgenic animals described herein can be produced according to the methods described in Wilmut et al. ((1997) Nature, 385:810–813) and PCT publication Nos. WO 97/07668 and WO 97/07669. In brief, a cell, e.g., a somatic cell from the transgenic animal, can be isolated and induced to exit the growth cycle and enter the $G_o$ phase to become quiescent. The quiescent cell can then be fused, e.g., through the use of electrical pulses, to an enucleated oocyte from an animal of the same species from which the quiescent cell is isolated. The reconstructed oocyte is then cultured such that it develops into a morula or blastocyte and is then transferred to a pseudopregnant female foster animal. Offspring borne of this female foster animal will be clones of the animal from which the cell, e.g., the somatic cell, was isolated.

Intronic sequences and polyadenylation signals can also be included in the transgene to increase the efficiency of expression of the transgene. A tissue-specific regulatory sequence(s) can be operably linked to a transgene of the invention to direct expression of a ZF-TetR protein to particular cells. A transgenic founder animal can be identified based upon the presence of a ZF-TetR transgene in its genome and/or expression of ZF-TetR mRNA in tissues or cells of the animals. A transgenic founder animal can then be used to breed additional animals carrying the transgene. Moreover, transgenic animals carrying a transgene encoding a ZF-TetR protein can further be bred to other transgenic animals carrying other transgenes.

ZF-TetR proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal.

EXAMPLES

The invention is further illustrated by the following examples. The examples are provided for illustration only, and are not to be construed as limiting the scope or content of the invention in any way.

Example 1

Creation of a Zinc Finger-Tet Repressor (ZF-TetR) Prototype Chimera

A prototype ZF-TetR chimera is designed using computer modeling to define fusion points between the zinc finger and Tet repressor domains that provides a DNA-binding chimera with the desired properties, and to explore the preferred spacing between the half-sites recognized by each monomer. The designed sequences aid in defining the preferred spacing of the half-sites that are recognized by the DNA-binding domain of each monomer in the context of the ZF-TetR dimer. The tetracycline-dependence for this prototype is then tested. This computer modeling provides a foundation from which highly sequence-specific, drug-dependent ZF-TetR chimeras can be selected by phage display.

A ZF-TetR fusion protein is designed that will bind as a dimer to a palidromic DNA sequence composed of the recognition sites for the incorporated zinc fingers. Structure-based design (e.g., as described in Pomerantz et al., "Structure-based design of a dimeric zinc finger protein," Biochemistry, 37, 965–70, 1998) is the first step in creating a functional ZF-TetR fusion protein. This involves superimposing the DNA in the DNA-bound structures of Zif268 (see, Elrod-Erickson et al., Structure, 4, 1171–1180, 1996) and Tet repressor (see, Orth et al., Nat. Struct. Biol., 7, 215–9, 2000), and then changing the relative register of the two proteins until there is close approach between the final recognition helix in Zif268 and the "joining" α-helix that connects the DNA-binding domain and dimerization domain in the Tet repressor. This initial modeling showed that a fusion between the Zif268 zinc fingers and the Tet repressor dimerization domain provides a functional dimer.

Subsequent structural analysis of the Zif268-GCN4 complex (Wolfe, S A; Grant, R A & Pabo, C O, unpublished results) revealed that the leucine zipper dimerization domain is actually rotated by ~30° along the $C_2$ axis of symmetry in the dimer relative to the zipper in the parent GCN4 complex. This result indicates that other orientations of the Tet repressor dimerization domain relative to the DNA can be used for a better overlap between the two structures, e.g., by rotating the Tet repressor dimerization domain ~45° relative to the $C_2$ axis of symmetry in the dimer (FIG. 7). Based on this model and additional work, a ZiF268-TetR chimera binds to DNA as a dimer and prefers a DNA sequence wherein the ZiF268 sites recognized by each monomer are separated by seven or eight base pairs (e.g., 5'-CCCACGCNNNNNNN-GCGTGGG-3' (SEQ ID NO:10) or 5'-CCCACGCNNNNNNNNGCGTGGG-3' (SEQ ID NO:3), where N is any DNA base).

Based on the computer modeling, prototype Zif268-TetR chimeras are constructed and tested for their ability to activate transcription in vivo. The fusion between the two domains is between the final histidine involved in zinc coordination in finger 3 of Zif268, and the first residue in the "joining" α-helix of the Tet repressor. Two different linker lengths between the final finger from Zif268 and the "joining" helix from tetR-DD can be used, consisting of either two or four glycine residues. The DNA encoding these chimeras are constructed by PCR, and consist of fingers 2 and 3 of Zif268, the glycine linker, and the "joining" α-helix and dimerization domains of a tet repressor.

The Tet repressor sequence used in this example is nucleotides 165–648 (encoding amino acids 48–207) of Genbank #X00694 (Class B; *E. coli* Tn10 tetR gene coding for tetR repressor) (SEQ ID NO:28). The zinc finger sequence used in this example is nucleotides 1291–1542 (encoding amino acids 333–416) of Zif268 (egr1; Mus musculus early growth response 1 (Egr1), mRNA, Genbank accession NM_007913) (SEQ ID NO:23).

These constructs are inserted into an expression vector that is compatible with a bacterial two-hybrid system, e.g., as described in Joung et al., Proc. Natl. Acad. Sci., USA., 97, 7382–7. (2000). This system is used to quantitatively assess the ill vivo DNA-binding specificity and affinity of the construct using three components: 1) a β-galactosidase reporter gene that is driven by a weak promoter with a binding site of interest placed upstream, 2) a DNA-binding domain (in this case the Zif268-TetR prototypes) fused to a fragment of Gal11P which serves as interaction domain to recruit a modified RNA polymerase, and 3) a modified RNA polymerase that contains a fusion between the alpha subunit and the Gal4 dimerization domain. If the Zif268-TetR prototypes recognize the binding site inserted in the promoter, they can recruit RNA polymerase through the Gal11P-Gal4 interaction, and thereby activate transcription. This system can be used to assess the ability of the Zif268-TetR prototypes to recognize binding sites with different half-sites spacings (number of base pairs between the sequence recognized by the zinc fingers in each monomer) in an *E. coli* strain lacking tetracycline resistance. This set of experiments is repeated in the presence of anhydrotetracycline (ATc), a tetracycline analogue that is not bactericidal, to determine if the construct displays drug-dependent DNA recognition. As a control the ability of a tet repressor-Gal11P fusion to activate transcription from a tetO containing promoter is examined in the presence and absence of ATc.

Example 2

Selection of ZF-TetR Clones that Bind to DNA

Clones that respond only in the absence of tetracycline (Tc), or only in the presence of Tc are identified. This creates the equivalent of a Tet-OFF (the absence of Tc) and Tet-ON (the presence of Tc) system, with the added advantage that the DNA-binding specificity of the zinc fingers call be changed to target DNA sequences within target genes, e.g., endogenous genes of interest. Phage display is used to select Zif268-TetR homodimers that bind DNA only in the presence or absence of tetracycline (Tc).

In general, the initial objective is to display the Zif268-TetR prototypes on fd bacteriophage and to characterize their retention on the preferred binding sites that were identified in Example 1, using the general methods described in Wolfe et al., Structure, 8, 739–750 (2000). The Zif268-TetR proteins are displayed as fusions to the phage coat protein gene III. The Zif268-TetR-gene In constructs consist of a N-terminal periplasmic export sequence, the coding sequence of the Zif268-TetR prototype, an amber codon to reduce the expression level of gene III fusions (to reduce problems associated with polyvalent effects), and the coding sequence of gene III. This construct is incorporated into a phagemid for expression in *E. coli*, and phage displaying this complex are made by infecting *E. coli* harboring this phagemid with VCS M13 helper phage (see, Rebar et al., Meth. Enzymol., 267, 129–149 (1996)). These phage are harvested, and their retention on specific and non-specific DNA binding sites bound to a solid support are tested. First biotinylated-DNA is attached to streptavidin-coated magnetic beads, and then magnetic eppendorf holders can be used to isolate the phage bound to the solid support from bulk solution. Phage displaying the full tet repressor are made to examine the tetracycline-dependence of DNA recognition for this homodimer on the surface of phage.

Two prototypes were constructed based on the computer modeling. These chimeras consisted of fingers 2 and 3 of Zif268 fused to the joining helix of the class B Tet repressor by a linker containing either 2 or 4 glycines using standard PCR techniques. These constructs were tested in a bacterial two-hybrid system for their ability to activate transcription of a LacZ reporter containing different half-site spacings (either 6, 7, 8 or 9 base pairs between the Zif268 binding sites). Experiments were performed in the absence or presence (100 ng/ml) of anhydrotetracycline (ATc), a tetracycline analogue that inhibits binding of Tet repressor but that is not bactericidal at low concentrations.

Briefly, expression vectors that encode these zinc finger libraries were constructed by introducing new restriction enzyme sites into the ZF-TetR-DD gene that allow a short synthetic DNA fragment to be ligated into the junction region to be randomized and varied in length. Using the synthetic DNA inserts, this junction region can be randomized and varied in length. Libraries of chimeras were generated by ligating the synthetic oligos into this region and electroporating these constructs into *E. coli*, XL1-blue strain. M13 phage were used to package these expression vectors for infection of KJ1C derived strains that harbor the desired target sequence in the promoter of a His3 reporter of the F' episome. Infected KJ1C cells (selected by one or more antibiotic markers) will be plated on selection media containing a desired concentration of 3-AT to establish the stringency of the selection (~$10^9$ cells/plate).

Colonies that grew under these conditions were be harvested, amplified, and the zinc finger constructs rescued by helper phage infection. The selection can be repeated to eliminate false positives that arise from colonies that develop spontaneous resistance to 3-AT. Colonies from the second round of selection were harvested and the zinc finger gene sequenced.

These chimeras weakly activated transcription of the LacZ reporter in the absence and in the presence of ATc, and there was no significant preference for the spacing of the half-sites (data not shown). Because the prototypes displayed only marginal DNA-binding specificity the next set of experiments focused on establishing whether ZF-TetR dimers could be created that display good DNA-binding specificity. Consequently, the bacterial two-hybrid system was used to select Zif268-TetR dimers with good DNA-binding specificity. Libraries were constructed in which the junction sequence between the Zif268 and TetR domains was randomized and varied in length (between 2 and 8 amino acids). These libraries were combined and screened in vivo against nucleic acid recognition sites that had 6, 7, 8, or 9 base pairs between the Zif268 binding sites. Selections were performed in the presence or absence of 1 μg/ml ATc in the selective media to screen for clones that bind only in the presence or only in the absence of the drug. Two rounds of selections were performed. Consensus sequences were observed for clones selected on the 7, 8, and 9 spaced sites in the absence of ATc (see Table 1). The sequences of clones from the other selections did not display any strong correlation.

The specificity of a single representative clone from the initial selections done on 7, 8, and 9 spaced sites in the absence of ATc was assayed using a LacZ reporter in the bacterial two-hybrid system. As shown in the graph of FIG. 5, these clones displayed a preference to activate transcription of the LacZ reporter only when a binding site with the appropriate half-site spacing was present, demonstrating desired specificity. Some weaker activation of half-sites separated by one additional or fewer base pairs was also observed. Similar levels of activation occurred in the absence or in the presence of ATc; thus these particular clones did not display significant drug-dependent behavior (data not shown), but did bind target DNA selectively.

In FIG. 5, the junction sequence of each clone is listed at the top of the panel (RASIMRR (SEQ ID NO:4), SVR-GRKVP (SEQ ID NO:5), and RKVNLP (SEQ ID NO:6). The left (gray), center (white), and right (black) clones were selected to recognize the 7, 8, and 9 base pair spacings, respectively.

Figure 6:
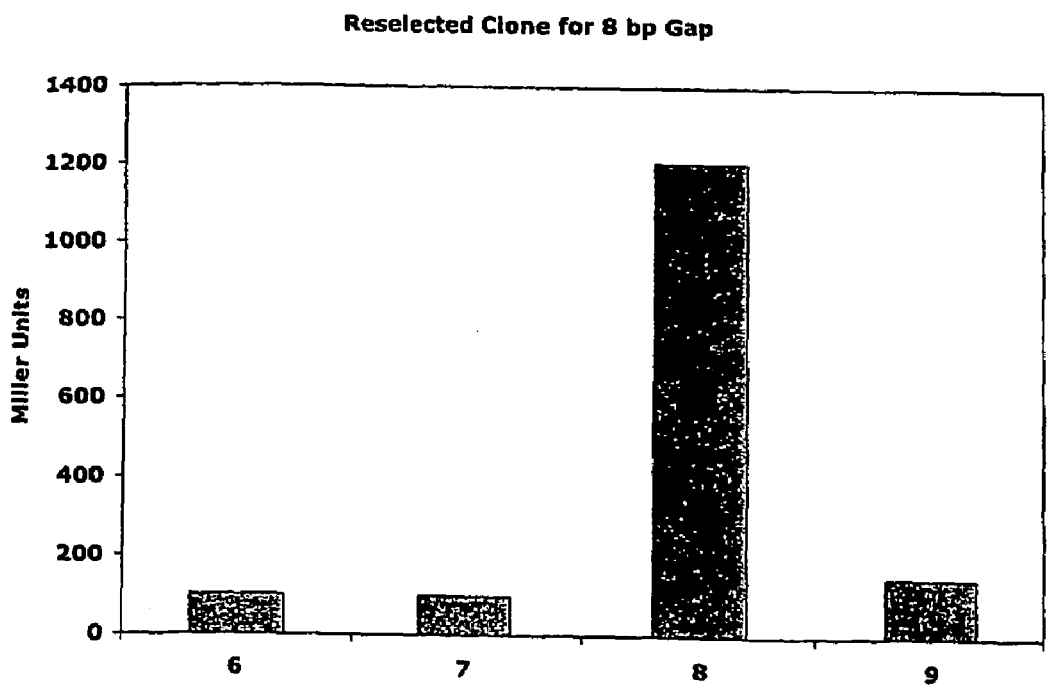
FIG. 6 is bar graph that illustrates activation of four different LacZ reporters by a reselected ZF-TetR clone. This particular clone was selected to recognize the 8 base pair gaped site, and demonstrates significant activation only for this spacing of the zinc finger target sites.

Additional rounds of selections were performed using a redesigned expression vector that contains a lac UV5 promoter weakened by two mutations in the —10 box (Whipple, Nucleic Acids Res., 1998, 26(16) 3700–3706), a zeocin resistance marker instead of ampicillin, and a weaker origin of replication (pACYC instead of ColE1) that allows a lower intracellular level of ZF-TetR protein expression to be established; thereby increasing the stringency of the selections. These selections provided clones with a higher degree of sequence specificity (FIG. 6). The four LacZ reporters have 6, 7, 8, or 9 base pairs between the Zif268 binding sites. This particular clone was selected to recognize the 8 base pair gaped site, and demonstrates significant activation only for this spacing of the zinc finger target sites.

Drug-dependent clones are prepared by attaching more of these new clones to the surface of M13 bacteriophage, and performing selections to isolate drug-dependent clones.

Example 3

Validation of the Selected ZF-TetR$^{OFF}$ and ZF-TetR$^{ON}$ Systems

The ZF-TetR$^{OFF}$ and ZF-TetR$^{ON}$ systems are tested both in vitro using gel shift assays, and in vivo. The in vivo tests involve examining the ability of this system to regulate the endogenous gene VEGF-A in cell culture assays. VEGF-A is an important factor in angiogenesis, and plays a fundamental role in tumor formation and growth.

For this gene regulation system to be valuable, the DNA binding specificity of the zinc fingers in the selected Zif268-TetR$^{OFF}$ and Zif268-TetR$^{ON}$ clones must be amenable to change, and these proteins need to function in eukaryotic systems.

Gel-shift experiments are used to determine the DNA-binding specificity and affinity of the selected Zif268-TetR$^{OFF}$ and Zif268-TetR$^{ON}$ clones. Proteins are expressed using the Promega TNT-Quick™ coupled transcription/translation system. Affinities are determined using gel-shift assays with $^{32}$P-radiolabeled DNA. Specificities are determined through competition experiments with non-specific DNA, and by using SELEX experiments to determine the preferred DNA-binding site for each protein. These in vitro studies provide a direct assessment of the specificity of the Zif268 fingers in the context of the Tet repressor dimerization domain.

Next the new Zif268-TetR$^{ON/OFF}$ constructs are compared to previously described zinc finger proteins that have been used for endogenous gene regulation of VEGF-A in cell culture assays as described in Liu et al., A. J. Biol. Chem., 276, 11323–34. (2001). This comparison is facilitated by mapping of the chromatin accessible regions that has been performed for the human VEGF-A promoter (Liu et al., 2001). This gene is of particular interest because of its key role in angiogenesis, and consequently the important role that it plays in tumor growth. Furthermore, this is a good model system for future experiments designed to evaluate the effectiveness of the ZF-TetR$^{ON/OFF}$ system in mice. VGEF is embryonic lethal when knocked out in mice, and the effects of VGEF gene knockout in postnatal mice has been characterized using the Cre-Lox system (see e.g., Carmeliet et al., Nature, 380, 435–9 (1996) and Gerber et al., Development, 126, 1149–59 (1999)). These studies provide a comparative assessment of the phenotypes observed in transgenic mice carrying a ZF-TetR$^{ON/OFF}$ protein designed to repress VGEF expression.

Zinc fingers that recognize desired target sequences within the VEGF-A promoter are selected using the bacterial two hybrid system described in Example 1. These zinc fingers are selected in the homodimeric context defined by the tet repressor dimerization domain. Briefly, fingers with novel specificity are selected by creating a library in which the key DNA-binding residues in a single finger are randomized. Because of library constraints, only a single finger at a time can be selected. Consequently, selections will begin with the outer finger, and then a second round of selections will be used to change the specificity of the inner finger. Selections are performed by introducing a section of the appropriate target site from the VGEF-A promoter upstream of the His3 reporter in the bacterial selection system. The ZF-TetR library is introduced into cells containing the His3 reporter, and the cells are plated on media lacking histidine. The stringency of the selection is adjusted by titering in the competitive inhibitor 3-amino-triazole to obtain clones with the desired DNA-binding specificity. These selections are performed in the presence of ATc when the zinc finger selections are performed in the context of the Zif268-TetR$^{ON}$ protein.

The objective of the selections is to generate components that in combination create functional heterodimers that recognize a region of the VGEF-A promoter. Two constructs, each comprising a monomer of the ZF-TetR heterodimer, are tested together for their ability to activate transcription in the bacterial two hybrid β-galatosidase assay described in Example 1. These constructs are also tested for drug-dependent DNA recognition by performing the experiments in the presence and absence of ATc. Constructs are also tested individually to ensure that any activation that is observed is the result of heterodimer formation, and not the result of the homodimers of each individual construct that also can form.

Functional heterodimers are then tested as VP-16 fusions in HEK293 cells for their ability to activate transcription of the endogenous VGEF-A gene, and the levels of activation are compared to previously described zinc finger proteins that recognize the same regions of the promoter, which are independently assayed. Two constructs, each comprising a monomer of the ZF-TetR heterodimer, are introduced by transient transfection into the HEK293 cells. VEGF-A expression in these cells is assayed using a VGEF-A ELISA kit (R & D Systems) and quantitative RT-PCR. ZF-TetR constructs can also be tested individually to ensure that any activation that is observed is the result of heterodimer formation.

Example 4

Creation of Transgenic Mouse Lines Containing ZF-TetR$^{OFF}$ and ZF-TetR$^{ON}$ Proteins Specific for the VGEF-A Gene This will allow an assessment of the feasibility of using this system to create functional knockouts in mice with temporal control. Because the Tet-ON/OFF systems have already been used successfully in mice, these new systems will function as well.

Gene knockout mice are created by interrupting a single allele of the gene of interest in embryonic stem (ES) cells, creating chimeric animals using these ES cells, and then creating F1 progeny from the chimera (see, e.g., Williams et al., 2000, J. Appl. Physiol., 88:1119–1126). Using the ZF-TetR-DD system, repression of both alleles of a gene is accomplished by tailoring the zinc fingers in this drug-regulatable system to recognize a target sequence in the promoter of the gene of interest, and attaching a KRAB repression domain using a spacer of about 5 to 10 amino acids. The transgenic mice that express this construct require only the non-specific integration of a single construct, and thus provide a more efficient method for creating a functional "knockout" mouse that is "knocked out" on command by the addition of Tc.

The ZF-TetR$^{ON/OFF}$ proteins used to create successful functional knockouts, demonstrate that this system can be used generally with respect to genes that can be targeted in mice, or in other eukaryotic model systems.

Example 5

Crystallization and Structure-Determination of the Zif268-TetR$^{OFF}$ and Zif268-TetR$^{ON}$ Protein-DNA Complexes To provide information at the molecular level regarding interactions between the Tet repressor fused zinc fingers and the DNA to which they bind, structural studies are performed using standard techniques. Such studies permit an assessment of potential deficiencies introduced into the system in the formation of this chimera. This provides information for altering the structures to optimize their performance, and can be used as an additional step in selection and designing the constructs and sequences of the invention (e.g., to improve their functionality).

Crystallization and structure determination of Tet repressor fused zinc fingers (bound to DNA and/or unbound) is performed using methods known in the art and described herein. Briefly, the ZF-TetR-DD protein is overexpressed in E. coli and purified. The oligonucleotide that contains the desired target sequence is synthesized using standard phosphoramidite chemistry. All crystallization steps are carried out in an anaerobic chamber ([O2]~1 ppm) to avoid oxidation of the cysteines. Prior to complex formation, the protein is concentrated to a concentration of 1.9 mM with 1.5 equivalents/finger $CoCl_2$ in 80 mM Bis-Tris Propane (pH 8.0). The protein-DNA complex is then formed by mixing 12.5 ml of refolded protein with 237.5 ml of duplex DNA (0.056 mM) in 10 mM Bis-Tris Propane (pH 8.0), 1 mM $MgCl_2$. This reaction is allowed to equilibrate overnight and is then subsequently centrifuged to remove any precipitate. Crystals are grown using hanging drop vapor diffusion: 3.2 ml of complex is allowed to equilibrate over a well solution containing ~600 mM NH4OAc. See, e.g., Wolfe et al., Structure, 2001, 9, 717–723.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A fusion polypeptide that regulates a target gene, consisting of:
   a first portion consisting of one or more zinc finger monomers comprising an amino acid sequence that binds to a nucleic acid recognition sequence in the target gene;
   a second portion consisting of a dimerization domain of a tetracycline repressor linked to the first portion such that the one or more zinc finger monomers can bind to the recognition sequence in the target gene, wherein the second portion is optionally linked to the first portion via a junction sequence; and
   a third portion consisting of an accessory domain that modulates a promoter operably linked with the target gene, wherein the accessory domain is linked to the zinc finger monomer such that the accessory domain is localized to the promoter when the zinc finger monomer binds to the recognition sequence, wherein the third portion is optionally linked to the first portion via a flexible junction sequence.

2. The fusion polypeptide of claim 1, wherein at least one of the zinc finger monomers comprises a portion of a Zif268 zinc finger.

3. The fusion polypeptide of claim 1, wherein at least one of the zinc finger monomers comprises amino acids 333–416 of Zif268 (SEQ ID NO:3); an amino acid sequence that binds to a TATA box; amino acids 498–560 of a *Drosophila* Tramtrak protein (SEQ ID NO:25); or amino acids 1 to 87 of artificial zinc finger protein MEY (SEQ ID NO:26).

4. The fusion polypeptide of claim 1, wherein the dimerization domain comprises amino acids 48–207 of an *E. coli* Tn10 Tet repressor (SEQ ID NO:28); amino acids 48–212 of a class E *E. coli* Tet repressor (SEQ ID NO:30); amino acids 48–218 of *E. Coli* Tet repressor RA1 (SEQ ID NO:31); amino acids 48–216 of a Class A *E. coli* Tet repressor (SEQ ID NO:32); or amino acids 48–219 of a Class C *E. Coli* Tet repressor (SEQ ID NO:33).

5. The fusion polypeptide of claim 1, wherein the dimerization domain comprises a pocket to which tetracycline binds to induce a conformational change of the fusion polypeptide that alters an ability of the zinc finger domain to bind to the recognition sequence.

6. The fusion polypeptide of claim 5, wherein binding of tetracycline to the pocket in the dimerization domain prevents the zinc finger monomer from binding to the recognition sequence.

7. The fusion polypeptide of claim 5, wherein binding of tetracycline to the pocket in the dimerization domain enables the zinc finger monomer to bind to the recognition sequence.

8. The fusion polypeptide of claim 1, wherein the second portion is linked to the first portion by a junction sequence.

9. The fusion polypeptide of claim 8, wherein the junction sequence comprises a sequence of 4 to 12 amino acids.

10. The fusion polypeptide of claim 8, wherein the junction sequence comprises an amino acid sequence of 6 to 8 amino acids.

11. The fusion polypeptide of claim 8, wherein the junction sequence comprises an amino acid sequence comprising 7 amino acids having the sequence Xaa (Ile or Val) Xaa (Gly or Ala) Arg Xaa Xaa (SEQ ID NO:7), wherein Xaa is any amino acid.

12. The fusion polypeptide of claim 1, wherein the recognition sequence is located in the vicinity of a promoter in the target gene.

13. The fusion polypeptide of claim 1, wherein the accessory domain comprises a repression domain.

14. The fusion polypeptide of claim 13, wherein the repressor domain comprises a Kruppel-associated box (KRAB) repression domain.

15. The fusion polypeptide of claim 1, wherein the accessory domain comprises an activation domain.

16. The fusion polypeptide of claim 15, wherein the activation domain comprises a VP16 activation domain.

17. A dimer comprising two fusion polypeptides of claim 1.

* * * * *